United States Patent
Dasse

(10) Patent No.: US 10,080,755 B2
(45) Date of Patent: Sep. 25, 2018

(54) DEUTERATED ANALOGS OF ETIFOXINE, THEIR DERIVATIVES AND USES THEREOF

(71) Applicant: Anvyl, LLC, Irvine, CA (US)

(72) Inventor: Olivier Dasse, Foothill Ranch, CA (US)

(73) Assignee: ANVYL, LLC, Irvine, CA (US)

( * ) Notice: Subject to any disclaimer, the term of this patent is extended or adjusted under 35 U.S.C. 154(b) by 0 days.

(21) Appl. No.: 15/557,748

(22) PCT Filed: Mar. 18, 2016

(86) PCT No.: PCT/US2016/023231
§ 371 (c)(1),
(2) Date: Sep. 12, 2017

(87) PCT Pub. No.: WO2016/154039
PCT Pub. Date: Sep. 29, 2016

(65) Prior Publication Data
US 2018/0064717 A1    Mar. 8, 2018

Related U.S. Application Data

(60) Provisional application No. 62/135,979, filed on Mar. 20, 2015.

(51) Int. Cl.
| | |
|---|---|
| A61K 31/536 | (2006.01) |
| A61K 31/03 | (2006.01) |
| C07D 265/18 | (2006.01) |
| C07B 59/00 | (2006.01) |
| A61K 31/015 | (2006.01) |

(52) U.S. Cl.
CPC .......... *A61K 31/536* (2013.01); *A61K 31/015* (2013.01); *A61K 31/03* (2013.01); *C07B 59/002* (2013.01); *C07D 265/18* (2013.01); *A61K 2300/00* (2013.01)

(58) Field of Classification Search
CPC ................................................... A61K 31/536
USPC ........................................................ 544/90
See application file for complete search history.

(56) References Cited

U.S. PATENT DOCUMENTS

| | | | |
|---|---|---|---|
| 8,338,410 | B2 | 12/2012 | Verleye et al. |
| 9,872,858 | B2 | 1/2018 | Verleye et al. |
| 2008/0038331 | A1 | 2/2008 | Putman et al. |

OTHER PUBLICATIONS

Aouad, M. et al. "Etifoxine stimulates allopregnanolone synthesis in the spinal cord to produce analgesia in experimental mononeuropathy" Eur. J Pain 18 (2014) 258-268; copyright 2013 European Pain Federation—EFIC, doi:10.11002/j.1532-2149.2013.00367.x.

Aouad, Mary et al., "Reduction and prevention of vincristine-inducted neuropathic pain symptoms by the non-benzodiazepine anxiolytic etifoxine are mediated by 3α—reduced neurosteroids" PAIN 147 (2009) 54-59.

Aouad, Maya et al., "Etifoxine analgesia in experimental monoarthritis: A combined action that protects spinal inhibition and limits central inflammatory processes" PAIN 155 (2014) 403-412.

Juif, P.E. et al. "Characterization of the fast GABAergic inhibitory action of etifoxine during spinal nociceptive processing in male rats" Neuropharmacology (2014) http://dx.doi.org/10.1016/j.neuropharm.2014.12.022.

Lysenko, G. et al., "Treatment of Anxiety in Patients with Chronic Joint Pain", National Medical Academy of Post Graduation Education named after P.L. Shupyk, Department of Family Medicine, Kyiv, Ukraine, date unknown.

PUBCHEM, Substance Record for SID 162262924, Date unknown. Retrieved from the Internet. https://pubchem.ncbi.nlm.nih.gov/substance/162262924/version/1#section=Top.

PUBCHEM, Substance Record for SID 162262925, Date unknown. Retrieved from the Internet. https://pubchem.ncbi.nlm.nih.gov/substance/162262925/version/1#section=Top.

Zeitler, Alexandre et al., "Favoring inhibitory synaptic drive mediated by GABA, receptors in the basolateral nucleus of the amygdala efficiently reduces pain symptoms in neuropathic mice" Centre National de la Recherche Scientifique and University of Strasbourg, Institute for Cellular and Integrative Neuroscience (INCI), F-67084, Strasbourg, France, doi: 10.1111/ejn.13217, date unknown.

*Primary Examiner* — Nizal S Chandrakumar
(74) *Attorney, Agent, or Firm* — Adler Pollock & Sheehan P.C.; Daniel J. Holmander, Esq.

(57) ABSTRACT

This invention relates to deuterated analogs of etifoxine of Formula 1, solvates, prodrugs, and pharmaceutically acceptable salts thereof, as well as to methods for their preparation and use, and to pharmaceutical compositions. Briefly, this invention is generally directed to deuterated analogs of etifoxine as well as to methods for their preparation and use, and to pharmaceutical compositions containing the same.

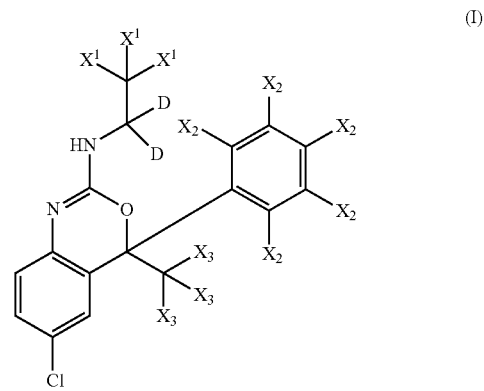

17 Claims, 1 Drawing Sheet

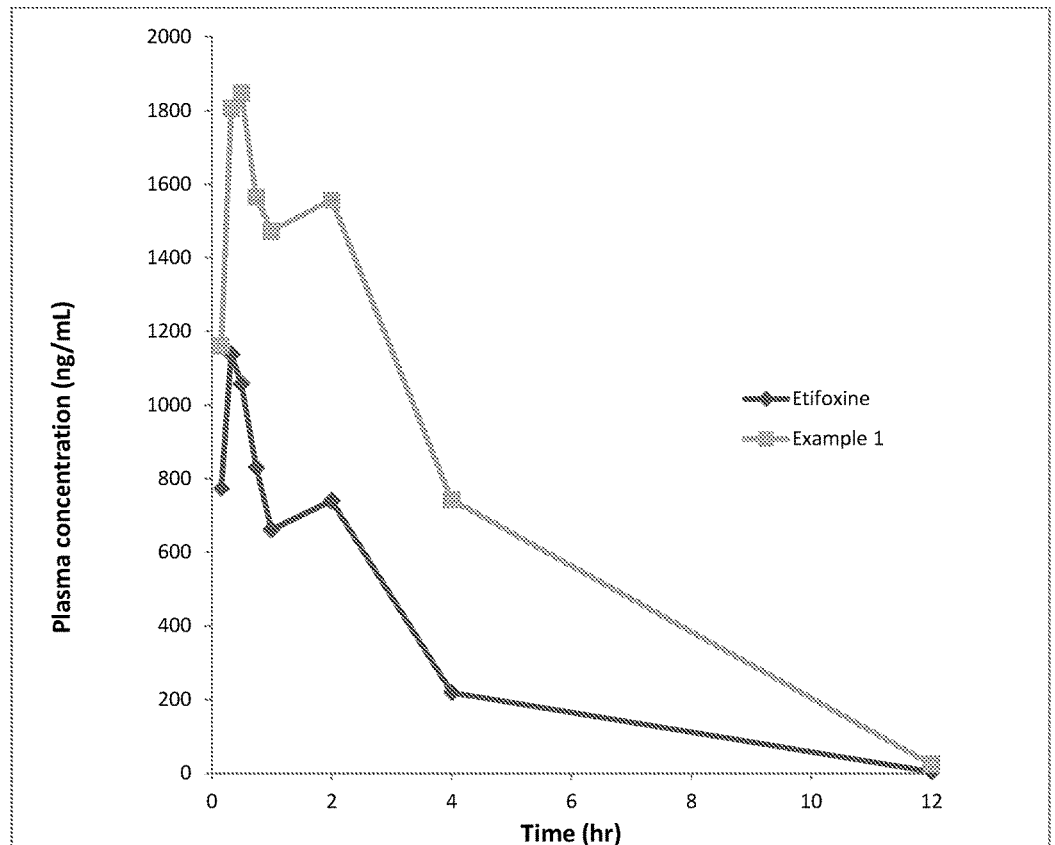
Mean plasma concentration-time profiles of etifoxine and example 1 after a PO dose of 50 mg/kg in male Sprague-Dawley rats

DEUTERATED ANALOGS OF ETIFOXINE, THEIR DERIVATIVES AND USES THEREOF

CROSS REFERENCE TO RELATED APPLICATIONS

This application is a national phase filing under 35 U.S.C. § 371 of International Application No. PCT/US2016/023231 filed Mar. 18, 2016, which claims priority from Spain application number 62/135,979, filed Mar. 20, 2015 the entire contents of which is hereby incorporated by reference herein.

BACKGROUND OF THE INVENTION

Adsorption, distribution, metabolism and excretion (ADME) properties of drugs are critical characteristics of any drug and can mean the difference between a safe and effective drug on the one hand, and a clinical and commercial failure, on the other hand. While recent advances in drug formulation technologies (and drug conjugates or prodrugs) have offered some ability to improve ADME in limited cases, underlying ADME problems are still a major cause of the failure of drugs in clinical trials. A common ADME issue with currently approved drugs and drug candidates is rapid metabolism. A drug candidate that otherwise is highly efficacious in in vitro and preclinical testing, can be metabolized too quickly and cleared from the body giving little to no pharmacological effect. "Band Aid" efforts to overcome fast metabolism include dosing at very high levels or dosing very frequently. Both of these solutions to rapid metabolism are fraught with problems, including increasing the side effects of drugs, increasing exposure to toxic metabolites, and decreasing patient dosing compliance due to frequency.

In limited cases, metabolic inhibitors have been used to improve the characteristics of a particular drug (see Kempf, D. et al. Antimicrobial Agents and Chemotherapy, 41(3), p. 654 (1997); Wang, L. et al. Clinical Pharmacology and Therapeutics, 56(6 Pt. 1), p. 659 (1994). However, this strategy is not widely used, and can lead to serious unwanted side effects, and undesired drug-drug interactions.

Optimization of drug structure by chemists usually involves an iterative process of structure modification to improve biological activity and/or metabolic properties. However, a better metabolic profile often comes at the expense of biological potency and efficacy, due to the significant structural modifications of a desired pharmacophore structure needed to stop or slow biological degradation processes. A potential strategy for improving the metabolic profile of a drug, without substantially altering the biological potency and efficacy, is to replace (substitute) one or more hydrogen atoms with deuterium, thus slowing cytochrome P450 mediated metabolism. Deuterium is an isotope of hydrogen that contains an additional neutron in its nucleus, and is safe, stable and nonradioactive. Due to the increased mass of deuterium as compared to hydrogen, the bond between carbon and deuterium has a higher energy (stronger) as compared to the bond between hydrogen and carbon, and can reduce metabolic reactions rates. The reduced metabolic reaction rate can favorably impact a molecule's ADME properties, giving improved potency, efficacy, safety and tolerability. Other physical characteristics of deuterium are essentially identical to hydrogen, and would not be expected to have a biological impact on a molecule with deuterium replacement.

In nearly four decades, only a small number of drugs have been approved that employ deuterium substitution to improve metabolism (see Blake, M. et al. J. Pharm. Sci., 64, p. 367 (1975); Foster, A. Adv. Drug Res., 14, p. 1 (1985); Kushner, D. et al. Can. J. Physiol. Pharmacol., p. 79 (1999); Fisher M. et al. Curr. Opin. Drug Discov. Devel., 9, p. 101 (2006)). The result of deuterium replacement of hydrogen on metabolic rate, however, has not been predictable and has led to variable results. In some cases the deuterated compounds had a decreased metabolic clearance in vivo, however for others, there was no change in the clearance rate, and yet others unexpectedly showed an increase in metabolic clearance rate. This variability has led ADME experts to question or reject deuterium replacement as a strategic drug design modification for reducing metabolic rate (see Foster and Fisher).

Even when a site and position of metabolism is known, deuterium replacement does not have a predictable effect on the metabolic rate. It is only by preparation of the specific deuterium substituted drug (candidate) and testing that one can determine the extent of change in metabolic rate. See Fukuto, J. et al. J. Med. Chem., 34(9), p. 2871 (1991). Many, if not most, drug candidates have multiple sites where metabolism is possible, however, this is unique to each drug molecule, thus making deuterium replacement a different study for its effect on each candidate. See Harbeson, L. and Tung, R. Medchem News, 2, p. 8 (2014) and references therein. There are several examples of drug candidates where deuterium substitution of hydrogen has led to an enhanced metabolic rate and/or metabolic switching, or no in vivo change of the molecule's profile even after metabolic slowing. Harbeson et al. reveal that selective deuteration of paroxetine at predicted metabolically labile positions actually produced analogs which demonstrated increased metabolism in vivo (Scott L. Harbeson and Roger D. Tung, Deuterium in Drug Discovery and Development, 46 annual report in medicinal chemistry, 403-417 (2011)). Furthermore, Miwa reports that deuteration of metabolically labile sites may lead to the potentiation (or switching) of alternative metabolic pathways, with then undetermined consequences (Miwa, G., Lu, A., Kinetic Isotope Effects and 'Metabolic Switching' in Cytochrome P450-Catalyzed Reactions, 7 Bioessays, 215-19 (1987)). Phentermine has been deuterated to decrease its metabolic rate, however replacement of N,N-dimethyl hydrogens with deuterium resulted in no change observed (Allan B. Foster, "Deuterium Isotope Effects in the Metabolism of Drugs and Xenobiotics: Implications for Drug Design", Advances in Drug Research, (14), 1-40 (1985)). Similarly, deuteration of metabolically active sites of tramadol led to no increase in duration of effect (Shao et. al., "Derivatives of Tramadol for Increased Duration of Effect", Bioorganic and Medicinal Chemistry Letters, (16), 691-94 (2006)).

Etifoxine [6-chloro-2-(ethylamino)-4-methyl-4-phenyl-4H-3,1-benzoxazine] was originally disclosed in U.S. Pat. No. 3,725,404 by Hoffmann, I et al. Etifoxine has been shown to be an effective, acute acting, anxiolytic agent in humans with minimal sedative and ataxic side effects. Stein, D., Adv. Ther. 32(1), p. 57 (2015); Nguyen, N. et al., Hum. Psychopharm. 21, p. 139 (2006); Micallef, J., Fundam. Clin. Pharmacol., 15(3), p. 209 (2001).

The hydrochloride salt of etifoxine [6-chloro-2-(ethylamino)-4-methyl-4-phenyl-4H-3,1-benzoxazine] is known as Stresam™ and is sold mainly in France and in a limited number of other markets around the world for the treatment of anxiety (specifically, anxiety with somatic manifestations). The short half-life of etifoxine in humans (4-6 hours) is a significant limitation in its use. The recommended dosing schedule for etifoxine is three times a day (or a higher dose, twice a day). This schedule can be quite inconvenient to the patient and can contribute to dosing noncompliance. See Santana, L. et al, Patient Preference and Adherence, 5, p. 427 (2011). Studies also show a significant individual variability of the pharmacokinetic parameters especially in the dose $C_{max}$ relationship. (see etifoxine package insert information, Lundbeck Argentina SA). Inter and intra-patient variability is largely based on differences in drug metabolic capacity. Reducing inter and intra-patient variability is desirable as it hampers optimal therapy. Poor metabolizers may be at higher risk of off-targets side-effects due to higher drug levels. Excessive metabolizers may not get relief from insufficient efficacy due to excessively diminished drug levels. (see Wilkinson, G. The New England Journal of Medicine (352), 2211-21 (2005). Enhancing the metabolic stability of etifoxine will reduce inter- and intra-patient variability as metabolic capacity becomes less of a determining factor.

Consequently, despite the desirable and beneficial effects of etifoxine, the requirements for multiple daily dosing and significant drug level patient variability limit its advantages. Thus, there is a continuing need for new compounds to treat the aforementioned diseases and conditions.

SUMMARY OF THE INVENTION

Briefly, this invention is generally directed to deuterated analogs of etifoxine as well as to methods for their preparation and use, and to pharmaceutical compositions containing the same. More specifically, the deuterated analogs of etifoxine of this invention are compounds represented by the general structure:

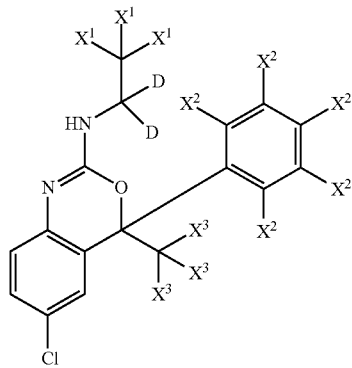

I including pharmaceutically acceptable salts, solvates, and prodrugs thereof, wherein each $X^1$, $X^2$, $X^3$ are independently selected from the group consisting of hydrogen and deuterium.

The present invention also is directed to pharmaceutical formulations which include a compound of Formula I, pharmaceutically acceptable salts, solvates, and prodrugs thereof, and one or more pharmaceutically acceptable excipients, carriers or diluents. Such formulations contain a therapeutically effective amount of a compound of Formula I, pharmaceutically acceptable salts, solvates, and prodrugs thereof, and one or more pharmaceutically acceptable excipients, carriers or diluents.

The present invention is also directed to pharmaceutical compositions for the treatment of conditions amenable to modulation of the $GABA_A$ receptor complex; or increasing endogenous neurosteroid and neuroactive steroid levels; CNS disorders; PNS disorders; or inflammatory conditions comprising administering to a subject in need of such treatment a therapeutically effective amount of a compound of Formula I, and pharmaceutically acceptable salts, solvates, and prodrugs thereof.

The present invention is also directed to the use of compounds of Formula I, pharmaceutically acceptable salts, solvates, and prodrugs thereof to treat conditions amenable to modulation of the $GABA_A$ receptor complex; or increasing endogenous neurosteroid and neuroactive steroid levels; CNS disorders; PNS disorders; or inflammatory conditions as described more fully below in subjects in need of such therapy comprising administering a therapeutically effective amount of such compounds.

In another aspect, the invention also provides a kit comprising a therapeutically effective amount of a compound of Formula I, or a pharmaceutically acceptable salt, solvate, or prodrug thereof, and instructions for treating a human patient suffering from conditions amenable to modulation of the $GABA_A$ receptor complex; or increasing endogenous neurosteroid and neuroactive steroid levels; CNS disorders; PNS disorders; or inflammatory conditions as described more fully below.

Additional embodiments and advantages of the invention will be set forth in part in the description that follows, and in part will be apparent from the description, or may be learned by practice of the invention. The embodiments and advantages of the invention will be realized and attained by means of the elements and combinations particularly pointed out in the appended claims. It is to be understood that both the foregoing general description and the following detailed description are exemplary and explanatory only and are not restrictive of the invention, as claimed. All texts and references cited herein are incorporated by reference in their entirety.

BRIEF DESCRIPTION OF THE DRAWINGS

FIG. 1 depicts the mean plasma concentration-time profiles of etifoxine and the compound of Example 1 after a PO dose of 50 mg/kg in male Sprague-Dawley rats.

DETAILED DESCRIPTION

The present invention is directed to deuterated analogs of etifoxine that have the therapeutic effects of etifoxine but with surprisingly superior ADME properties.

Etifoxine has been studied extensively preclinically, and has demonstrated efficacy in many animal models of CNS and mental disorders such as anxiety, pain, inflammatory pain, nerve damage, Multiple Sclerosis, alcohol withdrawal, epilepsy and light-induced lesions of the retina. Verleye, M. et al., Pharmacol. Biochem. Behav., 82(4), p. 712 (2005); Ugale, R. et al., Brain Res., 12, p. 193 (2007); Verleye, M. et al., Alcohol, 43(3), p. 197 (2009); Aouad, M. et al., Pain, 147(1-3), p. 54 (2009); Girard, C. et al., J. Neuroendocrinol., 24(1), p. 71 (2012); Zhou, X. et al., Mol. Med. Rep., 8(1), p. 75 (2013); Aouad, M. et al., Eur. J. Pain, 18(2), p. 258 (2014); Aouad, M. et al., Pain, 155(2), p. 408 (2014); Zhou, X. et al., Muscle Nerve, 50(2), p. 235 (2014); Dai, T. et al., J. Reconstr. Microsurg., 30(6), p. 381 (2014); Juif, P. et al., Neuropharmacology, 91, p. 117 (2015), Verleye, M et al. WO 2015113991.

Etifoxine has been described in scientific literature to act through allosteric modulation of the $GABA_A$ ion channel complex as well as increasing the levels of endogenous neurosteroids and neuroactive steroids. Verleye, M. et al., Neuroreport., 10(15), p. 3207 (1999); Verleye, M. et al., Neurosci. Lett., 301(3), p. 191 (2001); Hamon, A. et al., Neuropharmacology, 45(3), p. 293 (2003); Ugale, R. et al., Brain Res., 12, p. 193 (2007); Verleye, M. et al., Pharmacol. Biochem. Behav., 82(4), p. 712 (2005).

Neurosteroids and neuroactive steroids have demonstrated anti-inflammatory activity, for instance progesterone and allopregnanolone reduce both cytokines IL-1β and TNF-α in a model of TBI (see He, J. et al. Experimental Neurology, 189, p. 404 (2004)). Furthermore, dehydroepiandosterone (DHEA), which is mainly synthesized in the adrenal glands, inhibits the synthesis of cytokines IL-6 and TNF (see Straub, R. Rheumatology, 39, p. 624 (1999). By increasing levels of neurosteroids and/or neuroactive steroids, it is thought that etifoxine may be effective in treating neuroinflammation, peripheral inflammation and a variety of inflammatory conditions.

Neurosteroids and neuroactive steroids have been shown to be neuroregenerative and neuroprotective in preclinical models, see Brinton, R. *Nature Reviews Endocrinology* 9, 241-250 (2013) and Borowicz, K. et. al. Frontiers in Endocrinology 2(50), P. 1 (2011). Likewise, etifoxine has also demonstrated neuroregenerative and neuroprotective effects preclinically (Girard et. al. Journal of Neuroendocrinology 24, 71-81 (2011), Girard et. al. Clinical and Experimental Pharmacology and Physiology 36, 655-661 (2009), Zhou et. al. *Muscle Nerve.* 50(2):235-43 (2014)).

While the present invention is not limited to a precise mechanism of action, deuterated analogs of etifoxine can be used in the treatment of conditions associated with the need for neuroprotection including neurodegeneration and neuroregeneration, and conditions associated with nerve degeneration and nerve dysfunction, as well as inflammatory conditions.

In one aspect, the present invention is directed to a compound of Formula I:

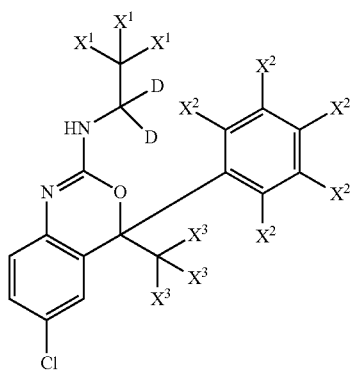

I and pharmaceutically acceptable salts, solvates, and prodrugs thereof, wherein: each of $X^1$, $X^2$ and $X^3$ is independently selected from the group consisting of hydrogen and deuterium.

Definitions

Unless specifically noted otherwise herein, the definitions of the terms used are standard definitions used in the art of organic synthesis and pharmaceutical sciences.

The articles "a" and "an" are used herein to refer to one or more than one (i.e. to at least one) of the grammatical object of the article. By way of example, "an element" means one element or more than one element.

As used herein, the term "or" is generally employed in the sense as including "and/or" unless the context of the usage clearly indicates otherwise.

Where the plural form is used for compounds, salts and the like, this is taken to mean also a single compound, salt, or the like.

As used herein "solvate" refers to a complex of variable stoichiometry formed by a solute (e.g. a compound of formula (I) or a salt, ester or prodrug thereof) and a solvent. Such solvents for the purpose of the invention may not interfere with the biological activity of the solute. Examples of suitable solvents include water, methanol, ethanol and acetic acid. Generally the solvent used is a pharmaceutically acceptable solvent. Examples of suitable pharmaceutically acceptable solvents include water, ethanol and acetic acid. Generally the solvent used is water.

"Isomers" mean any compound with an identical molecular formula but having a difference in the nature or sequence of bonding or arrangement of the atoms in space. Examples of such isomers include, for example, E- and Z-isomers of double bonds, enantiomers, and diastereomers. Compounds of the present invention depicting a bond with a straight line, unless specifically noted otherwise, is intended to encompass a single isomer and/or both isomers and means any compound with an identical molecular formula but having a difference in the nature or sequence of bonding or arrangement of the atoms in space.

The term "$GABA_A$ receptor" refers to a protein complex that detectably binds GABA and mediates a dose dependent alteration in chloride conductance and membrane polarization. Receptors comprising naturally-occurring mammalian (especially human or rat) $GABA_A$ receptor subunits are generally preferred, although subunits may be modified provided that any modifications do not substantially inhibit the receptor's ability to bind GABA (i.e., at least 50% of the binding affinity of the receptor for GABA is retained). The binding affinity of a candidate $GABA_A$ receptor for GABA may be evaluated using a standard ligand binding assay known in the art. There are a variety of $GABA_A$ receptor subtypes that fall within the scope of the term "$GABA_A$ receptor." These subtypes include, but are not limited to $\alpha_{1-6}$, $\beta_{1-3}$, $\gamma_{1-3}$, $\pi$, $\theta$, $\varepsilon$, $\delta$, and $\sigma_{1-3}$ receptor subtypes. $GABA_A$ receptors may be obtained from a variety of sources, such as from preparations of rat cortex or from cells expressing cloned human $GABA_A$ receptors. Particular subtypes may be readily prepared using standard techniques (e.g., by introducing mRNA encoding the desired subunits into a host cell).

As used herein, a "CNS disorder" is a disease or condition of the central nervous system that can be treated, prevented, managed or ameliorated with a compound or composition provided herein. Certain CNS disorders are responsive to $GABA_A$ receptor modulation in a subject and some CNS disorders are responsive to increasing endogenous neurosteroids and neuroactive steroids. Some CNS disorders include components where the Peripheral Nervous System ("PNS") is also compromised. Exemplary CNS disorders include multiple sclerosis, spinal muscular atrophy (believed to be due to loss of function of neuronal cells in the anterior horn of the spinal cord), muscle relaxation in spinal spasticity, cerebral palsy, trigeminal neuralgia, migraine, Alzheimer's disease, Huntington's chorea, Parkinson's disease, Creutzfeldt-Jakob's disease, Friedreich disease, retinal degenerations and photo-induced damage to the retina including photoretinitis, retinitis pigmentosa, age-related macular degeneration (AMD) and macular degeneration, delirium, dementia and amnestic and other cognitive disorders (delirium; dementia, such as dementia of Alzheimer's type, vascular dementia, dementia due to HIV disease, dementia due to head trauma, dementia due to Parkinson's disease, dementia due to Huntington's disease, dementia due to Pick's disease, dementia due to Creutzfeldt-Jakob disease, dementia due to general medical condition, substance-induced dementia, dementia due to multiple etiologies, dementia NOS (hereinafter "not otherwise specified" is abbreviated NOS); amnestic disorders, (such as amnestic disorder due to general medical condition, substance-induced amnestic disorder, amnestic disorder NOS; cognitive disorder NOS); ischemic or hemorrhagic cerebral vascular incidents including stroke and traumatic brain injury (TBI), phakomatoses (particularly neurofibromatosis), amyotrophic lateral sclerosis, schizophrenia, mood disorders (such as depressive disorder, including major depressive disorder-single episode or recurrent, dysthymic disorder, depressive disorder NOS; bipolar disorder, including. bipolar I disorder, bipolar II disorder, cyclothymic disorder, bipolar disorder NOS, mood disorder due to general medical condition, substance-induced mood disorder, mood disorder NOS), drug withdrawal symptoms, stuttering, autism, autism spectrum disorders, and convulsive disorders such as epilepsy. CNS disorders also includes mental disorders described in the American Psychiatric Association's Diagnostic and Statistical Manual of Mental Disorders, 5th edition (DSM-V) and include anxiety disorders (panic disorder without agoraphobia, panic disorder with agoraphobia, agoraphobia without history of panic disorder, specific phobia, social phobia, obsessive compulsive disorder, posttraumatic stress disorder, acute stress disorder, generalized anxiety disorder, anxiety disorder due to a medical condition, substance induced anxiety disorder, anxiety disorder not otherwise specified (NOS)), mood disorders, sleep disorders (primary sleep disorder, e.g. primary insomnia, primary hypersomnia, narcolepsy, breathing-related sleep disorder, circadian rhythm sleep disorder, dysomnia NOS; parasomnia, including. nightmare disorder, sleep terror disorder, sleepwalking disorder, parasomnia NOS; sleep disorder secondary to another mental disorder, e.g. sleep disorder secondary to anxiety, mood disorder and/or other mental disorder; sleep disorder due to general medical condition and substance-induced sleep disorder), attention deficit, attention deficit hyperactivity, and disruptive behavior disorders (attention deficit/hyperactivity disorder—combined type, predominantly inattentive type and predominantly hyperactive-impulsive type; attention deficit/hyperactivity disorder NOS; conduct disorder, oppositional defiant disorder and disruptive behavior disorder NOS) and substance related disorders. Mental disorders also include eating disorders such as anorexia and bulimia. Further mental disorders and criteria for those disorders are described in the American Psychiatric Association's Diagnostic and Statistical Manual of Mental Disorders, 5$^{th}$ edition (DSM-V), the contents of which are hereby incorporated by reference in their entirety.

As used herein, a "PNS disorder" is a disease or condition of the peripheral nervous system that can be treated, prevented, managed or ameliorated with a compound or composition provided herein. Certain PNS disorders are responsive to increasing endogenous neuroactive steroids. Some PNS disorders involve motor nerve and/or sensory nerve dysfunction and can include components where the spinal cord and/or the brain are also compromised. Exemplary PNS disorders include neuropathic disorders (neuropathic disorders include neuropathies associated with a metabolic disturbance such as diabetic neuropathy, drug-induced neuropathies such as alcohol induced neuropathy and vincristine-induced neuropathy, neuropathies associated with an inflammatory process as in Guillain-Barre syndrome, neuropathies associated with enzyme deficiency as in Fabry's disease and Krabbe's disease, peripheral neuropathy, infectious neuropathic conditions such as postherpetic and HIV-induced neuralgia, hereditary motor and sensory neuropathies such as Charcot-Marie-Tooth disease), and radiculoneuropathic diseases.

As used herein, a "neurodegenerative process" is characterized by the dysfunction and death of the neurons leading to the loss of the neurological functions mediated by the brain (CNS), the spinal cord and the PNS. They can result, amongst others, from pathological situations known collectively under the term of neurodegenerative diseases or affections, traumatism, or exposure to toxins.

As used herein, a "neuroprotective property" is the ability of a compound of the invention to treat a neurodegenerative process.

As used herein and unless otherwise indicated, the terms "neurosteroids" and "neuroactive steroids" refer to steroids naturally produced in a subject and alter neuronal excitability through interaction with ligand-gated ion channels and other cell surface receptors. Neurosteroids are produced in the brain. Neuroactive steroids are produced by conversion of peripherally-derived adrenal steroids or gonadal steroids. Examples of neurosteroids and neuroactive steroids are: pregnenolone, pregnanolone, allopregnanolone, tetrahydrodeoxycorticosterone, dehydroepiandrosterone and progesterone. Neuroactive steroids can have effects in the CNS and peripherally.

The term "treat" as used herein means decrease, reverse, suppress, attenuate, diminish, arrest, or stabilize the development or progression of a disease (including., a disease or disorder delineated herein), lessen the severity of the disease or improve the symptoms associated with the disease. In one aspect, treatment does not include prevention.

"Disease" means any condition or disorder that damages or interferes with the normal function of a cell, tissue, or organ.

As used herein "subject" is an animal, typically a mammal, including human, such as a patient.

As used herein, and unless otherwise specified, the terms "therapeutically effective amount" and "effective amount" of a compound refer to an amount sufficient to provide a therapeutic benefit in the treatment, prevention and/or management of a disease, to delay or minimize one or more symptoms associated with the disease or disorder to be treated. The terms "therapeutically effective amount" and "effective amount" can encompass an amount that improves overall therapy, reduces or avoids symptoms, or causes of disease or disorder, or enhances the therapeutic efficacy of another therapeutic agent.

The terms "co-administration" and "in combination with" include the administration of two therapeutic agents (for example, compounds of this invention and lorazepam) either simultaneously, concurrently or sequentially with no specific time limits. In one embodiment, both agents are present in a subject at the same time or exert their biological or therapeutic effect at the same time. In one embodiment, the two therapeutic agents are in the same composition or unit dosage form. In another embodiment, the two therapeutic agents are in separate compositions or unit dosage forms.

It will be recognized that some variation of natural isotopic abundance occurs in a synthesized compound depending upon the origin of chemical materials used in the synthesis. Thus, a preparation of etifoxine will inherently contain small amounts of deuterated isotopologues. The concentration of naturally abundant stable hydrogen and carbon isotopes, notwithstanding this variation, is small and immaterial as compared to the degree of stable isotopic substitution of compounds of this invention. See, for instance, Wada, E et al., Seikagaku, 1994, 66:15; Gannes, L Z et al., Comp Biochem Physiol Mol Integr Physiol, 1998, 119:725.

In the compounds of this invention, any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. Also, unless otherwise stated, when a position is designated specifically as "D" or "deuterium", the position is understood to have deuterium at an abundance that is at least 3340 times greater than the natural abundance of deuterium, which is 0.015% (i.e., at least 50.1% incorporation of deuterium).

The term "isotopic enrichment factor" as used herein means the ratio between the isotopic abundance and the natural abundance of a specified isotope. In some embodiments, a compound of this invention has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium), at least 5500 (82.5% deuterium incorporation), at least 6000 (90% deuterium incorporation), at least 6333.3 (95% deuterium incorporation), at least 6466.7 (97% deuterium incorporation), at least 6533 (98% deuterium incorporation), at least 6600 (99% deuterium incorporation), or at least 6633.3 (99.5% deuterium incorporation).

The term "isotopologue" refers to a species that differs from a specific compound of this invention only in the isotopic composition thereof.

The term "compound," when referring to a compound of this invention, refers to a collection of molecules having an identical chemical structure, except that there may be isotopic variation among the constituent atoms of the molecules. Thus, it will be clear to those of skill in the art that a compound represented by a particular chemical structure containing indicated deuterium atoms, will also contain lesser amounts of isotopologues having hydrogen atoms at one or more of the designated deuterium positions in that structure. The relative amount of such isotopologues in a compound of this invention will depend upon a number of factors including the isotopic purity of deuterated reagents used to make the compound and the efficiency of incorporation of deuterium in the various synthesis steps used to prepare the compound. However, as set forth above, the relative amount of such isotopologues in total will be less than 49.9% of the compound. In other embodiments, the relative amount of such isotopologues in total will be less than 47.5%, less than 40%, less than 32.5%, less than 25%, less than 17.5%, less than 10%, less than 5%, less than 3%, less than 1%, or less than 0.5% of the compound.

The term "pharmaceutically acceptable," as used herein, refers to a component that is, within the scope of sound medical judgment, suitable for use in contact with the tissues of humans and other mammals without undue toxicity, irritation, allergic response and the like, and are commensurate with a reasonable benefit/risk ratio. A "pharmaceutically acceptable salt" means any non-toxic salt that, upon administration to a recipient, is capable of providing, either directly or indirectly, a compound of this invention. A "pharmaceutically acceptable counterion" is an ionic portion of a salt that is not toxic when released from the salt upon administration to a recipient. Acids commonly employed to form pharmaceutically acceptable salts include inorganic acids such as hydrogen bisulfide, hydrochloric acid, hydrobromic acid, hydroiodic acid, sulfuric acid and phosphoric acid, as well as organic acids such as para-toluenesulfonic acid, salicylic acid, tartaric acid, bitartaric acid, ascorbic acid, maleic acid, besylic acid, fumaric acid, gluconic acid, glucuronic acid, formic acid, glutamic acid, methanesulfonic acid, ethanesulfonic acid, benzenesulfonic acid, lactic acid, oxalic acid, para-bromophenylsulfonic acid, carbonic acid, succinic acid, citric acid, benzoic acid and acetic acid, as well as related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephthalate, sulfonate, xylene sulfonate, phenylacetate, phenylpropionate, phenylbutyrate, citrate, lactate, .beta.-hydroxybutyrate, glycolate, maleate, tartrate, methanesulfonate, propanesulfonate, naphthalene-1-sulfonate, naphthalene-2-sulfonate, mandelate and other salts. In one embodiment, pharmaceutically acceptable acid addition salts include those formed with mineral acids such as hydrochloric acid and hydrobromic acid, and especially those formed with organic acids such as maleic acid. Standard methods for the preparation of pharmaceutically acceptable salts and their formulations are well known in the art, and are disclosed in various references, including for example, "Remington: The Science and Practice of Pharmacy", A. Gennaro, ed., 20th edition, Lippincott, Williams & Wilkins, Philadelphia, Pa.

The compounds of the present invention (including., compounds of Formula I), may contain an asymmetric carbon atom, for example, as the result of deuterium substitution or otherwise. As such, compounds of this invention can exist as either individual enantiomers, or mixtures of the two enantiomers. Accordingly, a compound of the present invention may exist as either a racemic mixture or a scalemic mixture, or as individual respective stereoisomers that are substantially free from another possible stereoisomer. The term "substantially free of other stereoisomers" as used herein means less than 25% of other stereoisomers, preferably less than 10% of other stereoisomers, more preferably less than 5% of other stereoisomers and most preferably less than 2% of other stereoisomers, or less than "X"% of other stereoisomers (wherein X is a number between 0 and 100, inclusive) are present. Methods of obtaining or synthesizing an individual enantiomer for a given compound are known in the art and may be applied as practicable to final compounds or to starting material or intermediates.

Unless otherwise indicated, when a disclosed compound is named or depicted by a structure without specifying the stereochemistry and has one or more chiral centers, it is understood to represent all possible stereoisomers of the compound.

The term "stable compounds," as used herein, refers to compounds which possess stability sufficient to allow for their manufacture and which maintain the integrity of the compound for a sufficient period of time to be useful for the purposes detailed herein (including., formulation into therapeutic products, intermediates for use in production of therapeutic compounds, isolatable or storable intermediate compounds, treating a disease or condition responsive to therapeutic agents).

"D" and "d" both refer to deuterium. Unless otherwise indicated, "stereoisomer" refers to both enantiomers and diastereomers.

The term "optionally substituted with deuterium" means that one or more hydrogen atoms in the referenced moiety may be replaced with a corresponding number of deuterium atoms.

The present invention includes prodrugs of the compounds of Formula I above. In general, such prodrugs will be functional derivatives of the compounds of Formula I that are readily convertible in vivo into the required compound of Formula I. Conventional procedures for the selection and preparation of suitable prodrug derivatives are described, for example, in Design of Prodrugs, ed. H. Bundgaard, Elsevier, 1985. Such prodrugs include but are not limited to ester prodrugs from alcohols and acids and phosphate prodrugs of alcohols. The prodrug can be formulation to achieve a goal of improved chemical stability, improved patient acceptance and compliance, improved bioavailability, prolonged duration of action, improved organ selectivity, improved formulation (including., increased hydrosolubility), and/or decreased side effects (including., toxicity).

Where the compounds of the present invention have at least one asymmetric center, they may accordingly exist as enantiomers. Where the compounds possess two or more asymmetric centers, they may additionally exist as diastereoisomers. Specifically, etifoxine exists as a racemic mixture and R-Etifoxine and S-Etifoxine have been prepared. U.S. Pat. No. 8,110,569. The present invention includes deuterated analogs of R-Etifoxine and deuterated analogs of S-Etifoxine. It is to be understood that all such stereoisomers and mixtures thereof in any proportion are encompassed within the scope of the present invention. Where the compounds possess geometrical isomers, all such isomers and mixtures thereof in any proportion are encompassed within the scope of the present invention. Tautomers of the compounds of the invention are encompassed by the present application. Thus, for example, a carbonyl includes its enol tautomer.

As used herein "pure S-etifoxine" are deuterated analogs that are is substantially free from deuterated R-etifoxine analogs (i.e., in enantiomeric excess). In other words, the "S" form of the deuterated etifoxine is substantially free from the "R" form of the compound and is, thus, in enantiomeric excess of the "R" form.

The term "enantiomerically pure" or "pure enantiomer" denotes that the compound comprises more than 75% by weight, more than 80% by weight, more than 85% by weight, more than 90% by weight, more than 91% by weight, more than 92% by weight, more than 93% by weight, more than 94% by weight, more than 95% by weight, more than 96% by weight, more than 97% by weight, more than 98% by weight, more than 98.5% by weight, more than 99% by weight, more than 99.2% by weight, more than 99.5% by weight, more than 99.6% by weight, more than 99.7% by weight, more than 99.8% by weight or more than 99.9% by weight, of the enantiomer. In certain embodiments, the weights are based upon total weight of the deuterated etifoxine analog.

As used herein and unless otherwise indicated, the term "enantiomerically pure R-etifoxine" refers to the deuterated analog that at least about 80% by weight deuterated R-etifoxine and at most about 20% by weight deuterated S-etifoxine, at least about 90% by weight deuterated R-etifoxine and at most about 10% by weight deuterated S-etifoxine, at least about 95% by weight deuterated R-etifoxine and at most about 5% by weight deuterated S-etifoxine, at least about 99% by weight deuterated R-etifoxine and at most about 1% by weight deuterated S-etifoxine, at least about 99.9% by weight deuterated R-etifoxine or at most about 0.1% by weight deuterated S-etifoxine. In certain embodiments, the weights are based upon total weight of deuterated etifoxine analog.

As used herein and unless otherwise indicated, the term "enantiomerically pure S-etifoxine" refers to at least about 80% by weight deuterated S-etifoxine and at most about 20% by weight deuterated R-etifoxine, at least about 90% by weight deuterated S-etifoxine and at most about 10% by weight deuterated R-etifoxine, at least about 95% by weight deuterated S-etifoxine and at most about 5% by weight deuterated R-etifoxine, at least about 99% by weight deuterated S-etifoxine and at most about 1% by weight deuterated R-etifoxine or at least about 99.9% by weight deuterated S-etifoxine and at most about 0.1% by weight deuterated R-etifoxine. In certain embodiments, the weights are based upon total weight of deuterated etifoxine analog.

Therapeutic Compounds

In one aspect, the present invention is directed to compounds of Formula IA:

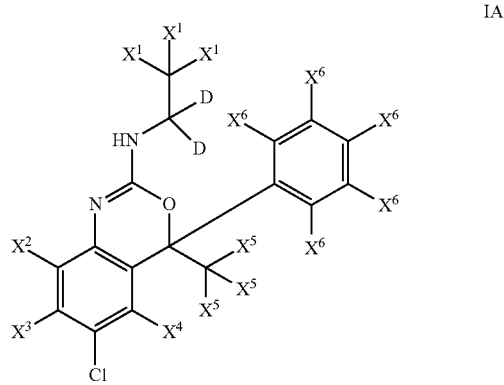

IA and pharmaceutically acceptable salts, solvates, and prodrugs thereof, wherein:

each $X^1$, $X^2$, $X^3$, $X^4$, $X^5$ and $X^6$ are independently selected from hydrogen and deuterium. In one embodiment, in such compounds each $X^1$ is deuterium.

In one embodiment of this invention, $X^2$, $X^3$, $X^4$, $X^5$ and $X^6$ are hydrogen such that the deuterated analog of etifoxine is a compound having the structure of Formula IIA:

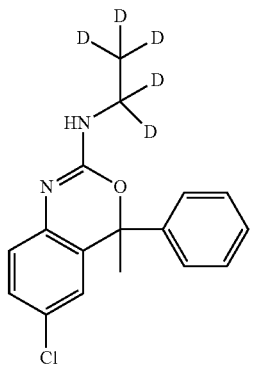

IIA and pharmaceutically acceptable salts, solvates, and prodrugs thereof.

In one embodiment, the compounds of Formula IA have each $X^1$ is hydrogen. In one such embodiment of this invention, $X^1$, $X^2$, $X^3$, $X^4$, $X^5$ and $X^6$ are hydrogen such that the deuterated analog of etifoxine is a compound having the structure of Formula IIIA:

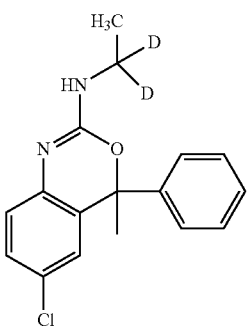

IIIA and pharmaceutically acceptable salts, solvates, and prodrugs thereof.

In one embodiment, the compounds of Formula IA have each $X^1$ and each $X^6$ as deuterium. In one such embodiment of this invention, $X^2$, $X^3$, $X^4$ and $X^5$ are hydrogen such that the deuterated analog of etifoxine is a compound having the structure of Formula IVA:

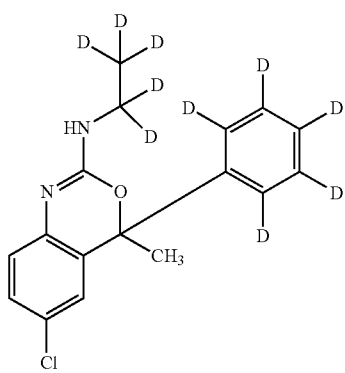

IVA and pharmaceutically acceptable salts, solvates, and prodrugs thereof.

In one embodiment, compounds of Formula IA have each $X^1$ and each $X^5$ are deuterium. In one such embodiment, $X^2$, $X^3$, $X^4$ and $X^6$ are hydrogen such that the deuterated analog of etifoxine is a compound having the structure of Formula VA:

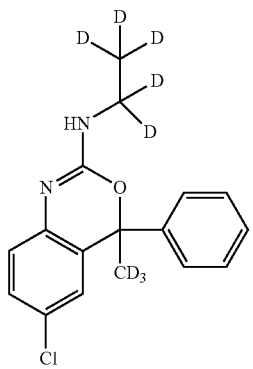

VA and pharmaceutically acceptable salts, solvates, and prodrugs thereof.

In one embodiment, compounds of Formula IA have each $X^1$, $X^2$, $X^3$, $X^4$, and $X^6$ are deuterium. In one such embodiment of this invention, $X^5$ and $X^6$ are hydrogen such that the deuterated analog of etifoxine is a compound having the structure of Formula VIA:

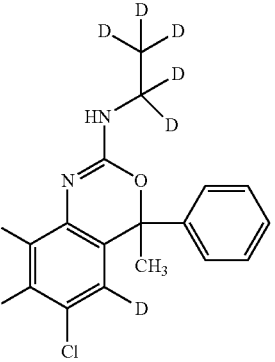

VIA and pharmaceutically acceptable salts, solvates, and prodrugs thereof.

In one embodiment of the invention, compounds of Formula IA have each $X^1$, $X^5$, and $X^6$ are deuterium. In one such embodiment of this invention, $X^2$, $X^3$ and $X^4$ are hydrogen such that the deuterated analog of etifoxine is a compound having the structure of Formula VIIA:

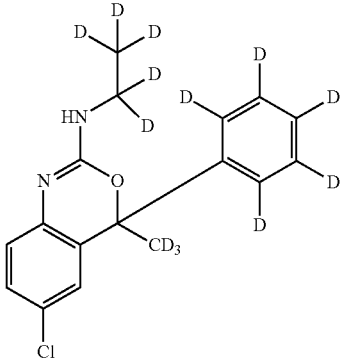

VIIA and pharmaceutically acceptable salts, solvates, and prodrugs thereof.

In one aspect, the present invention is directed to compounds of Formula I:

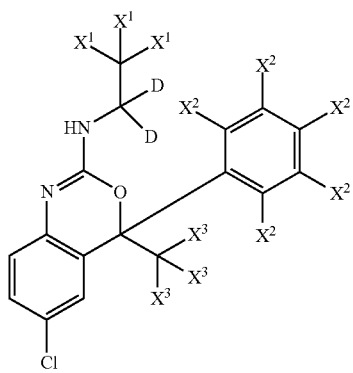

I and pharmaceutically acceptable salts, solvates, and prodrugs thereof, wherein: each of $X^1$, $X^2$ and $X^3$ are independently selected from hydrogen and deuterium. In one embodiment, in such compounds each $X^1$ is deuterium.

In one embodiment of this invention, each $X^2$ and $X^3$ are hydrogen such that the deuterated analog of etifoxine is a compound having the structure of Formula II:

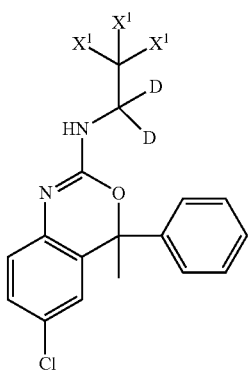

II and pharmaceutically acceptable salts, solvates, and prodrugs thereof.

In one embodiment of this invention the deuterated analog of etifoxine is 6-chloro-N-(ethyl-$d_5$)-4-methyl-4-phenyl-4H-3,1-benzoxazin-2-amine and pharmaceutically acceptable salts, solvates, and prodrugs thereof.

In another embodiment of this invention the deuterated analog of etifoxine is 6-chloro-N-(ethyl-$d_5$)-4-methyl-4-(phenyl-$d_5$)-4H-3,1-benzoxazin-2-amine and pharmaceutically acceptable salts, solvates, and prodrugs thereof.

In yet another embodiment of this invention the deuterated analog of etifoxine is 6-chloro-N-(ethyl-$d_5$)-4-(methyl-$d_3$)-4-(phenyl-$d_5$)-4H-3,1-benzoxazin-2-amine and pharmaceutically acceptable salts, solvates, and prodrugs thereof.

In yet another embodiment of this invention the deuterated analog of etifoxine is 6-chloro-N-(ethyl-1,1-$d_2$)-4-methyl-4-phenyl-4H-3,1-benzoxazin-2-amine and pharmaceutically acceptable salts, solvates, and prodrugs thereof.

In some embodiments, a compound of Formulae I-II; 6-chloro-N-(ethyl-$d_5$)-4-methyl-4-phenyl-4H-3,1-benzoxazin-2-amine; 6-chloro-N-(ethyl-$d_5$)-4-methyl-4-(phenyl-$d_5$)-4H-3,1-benzoxazin-2-amine; 6-chloro-N-(ethyl-$d_5$)-4-(methyl-$d_3$)-4-(phenyl-$d_5$)-4H-3,1-benzoxazin-2-amine; or 6-chloro-N-(ethyl-1,1-$d_2$)-4-methyl-4-phenyl-4H-3,1-benzoxazin-2-amine has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium), at least 5500 (82.5% deuterium incorporation), at least 6000 (90% deuterium incorporation), at least 6333.3 (95% deuterium incorporation), at least 6466.7 (97% deuterium incorporation), at least 6533 (98% deuterium incorporation), at least 6600 (99% deuterium incorporation), or at least 6633.3 (99.5% deuterium incorporation).

In one aspect, the compounds of Formulae I-II, are enantiomerically pure deuterated S-etifoxine isomer. In the compositions provided herein, deuterated enantiomerically pure S-etifoxine analog or a pharmaceutically acceptable salt, solvate, or prodrug thereof can be present with other active or inactive ingredients. For example, a pharmaceutical composition comprising deuterated enantiomerically pure S-etifoxine analog can comprise, for example, about 90% excipient and about 10% enantiomerically pure deuterated S-etifoxine analog. In certain embodiments, the enantiomerically pure S-etifoxine deuterated analog in such compositions can, for example, comprise, at least about 99.9% by weight S-etifoxine deuterated analog and at most about 0.1% by weight R-etifoxine deuterated analog. In certain embodiments, the active ingredient can be formulated with little or no excipient or carrier.

In one aspect, the compounds of Formulae I-II, are enantiomerically pure deuterated R-etifoxine isomer. In the compositions provided herein, deuterated enantiomerically pure R-etifoxine analog or a pharmaceutically acceptable salt, solvate, or prodrug thereof can be present with other active or inactive ingredients. For example, a pharmaceutical composition comprising deuterated enantiomerically pure R-etifoxine analog can comprise, for example, about 90% excipient and about 10% enantiomerically pure deuterated R-etifoxine analog. In certain embodiments, the enantiomerically pure R-etifoxine deuterated analog in such compositions can, for example, comprise, at least about 99.9% by weight R-etifoxine deuterated analog and at most about 0.1% by weight R-etifoxine deuterated analog. In certain embodiments, the active ingredient can be formulated with little or no excipient or carrier.

In another aspect, the compounds of the invention wherein any atom not designated as deuterium is present at its natural isotopic abundance.

In another aspect, there is provided pharmaceutical compositions comprising a pharmaceutically acceptable excipient and a compound of Formulae I-II, and pharmaceutically acceptable salts, solvates, and prodrugs thereof.

Methods of Treatment

In one embodiment, a compound of the invention of Formulae I-II, and pharmaceutically acceptable salts, solvates, and prodrugs thereof, is administered to a subject in an amount effective to modulate the $GABA_A$ receptor.

In one embodiment, a compound of the invention of Formulae I-II, and pharmaceutically acceptable salts, solvates, and prodrugs thereof, is administered to a subject in an amount effective to increase neurosteroids and/or neuroactive steroids.

In one embodiment, the compounds or composition of this invention acts as a modulator of $GABA_A$ receptor complex and increases endogenous neuroactive steroids and has anxiolytic, and/or anticonvulsant, and/or sedative/hypnotic, and/or anesthetic properties, and/or neuroprotective properties.

In certain embodiments, provided herein are methods of treating or preventing an etifoxine responsive condition comprising administering to a subject in need thereof a therapeutically effective amount of a compound of Formulae I-II, and pharmaceutically acceptable salts, solvates, and prodrugs thereof.

In one embodiment, compounds of Formulae I-II, and pharmaceutically acceptable salts, solvates, and prodrugs thereof are used to treat CNS disorders, PNS disorders, and/or inflammatory conditions by administering to a subject in need thereof a therapeutically effective amount.

In one embodiment, compounds of Formulae I-II, and pharmaceutically acceptable salts thereof are used to treat CNS disorders. In such embodiments, CNS disorders include multiple sclerosis, muscle relaxation in spinal spasticity, retinal degenerations and photo-induced damage to the retina including photoretinitis, retinitis pigmentosa, age-related macular degeneration (AMD) and macular degeneration, cerebral palsy, trigeminal neuralgia, migraine, Alzheimer's disease, Huntington's chorea, Parkinson's disease, Creutzfeldt-Jakob's disease, paraneoplastic polyneuritis, Friedreich disease, delirium, dementia and amnestic and other cognitive disorders (delirium; dementia, such as dementia of Alzheimer's type, vascular dementia, dementia due to HIV disease, dementia due to head trauma, dementia due to Parkinson's disease, dementia due to Huntington's disease, dementia due to Pick's disease, dementia due to Creutzfeldt-Jakob disease, dementia due to general medical condition, substance-induced dementia, dementia due to multiple etiologies, dementia NOS (hereinafter "not otherwise specified" is abbreviated NOS); amnestic disorders, (such as amnestic disorder due to general medical condition, substance-induced amnestic disorder, amnestic disorder NOS; cognitive disorder NOS); ischemic or hemorrhagic cerebral vascular incidents including stroke and traumatic brain injury (TBI), phakomatoses (particularly neurofibromatoses), amyotrophic lateral sclerosis, spinal muscular atrophy, schizophrenia, mood disorders (such as depressive disorder, including major depressive disorder—single episode or recurrent, dysthymic disorder, depressive disorder NOS; bipolar disorder, including. bipolar I disorder, bipolar II disorder, cyclothymic disorder, bipolar disorder NOS, mood disorder due to general medical condition, substance-induced mood disorder, mood disorder NOS), drug withdrawal symptoms, stuttering, autism, autism spectrum disorders, convulsive disorders such as epilepsy; anxiety disorders (panic disorder without agoraphobia, panic disorder with agoraphobia, agoraphobia without history of panic disorder, specific phobia, social phobia, obsessive compulsive disorder, posttraumatic stress disorder, acute stress disorder, generalized anxiety disorder, anxiety disorder due to a medical condition, substance induced anxiety disorder, anxiety disorder not otherwise specifed (NOS)), mood disorders, sleep disorders (primary sleep disorder, including. primary insomnia, primary hypersomnia, narcolepsy, breathing-related sleep disorder, circadian rhythm sleep disorder, dyssomnia NOS; parasomnia, including. nightmare disorder, sleep terror disorder, sleepwalking disorder, parasomnia NOS; sleep disorder secondary to another mental disorder, including sleep disorder secondary to anxiety, mood disorder and/or other mental disorder; sleep disorder due to general medical condition and substance-induced sleep disorder), attention deficit, attention deficit hyperactivity, and disruptive behavior disorders (attention deficit/hyperactivity disorder—combined type, predominantly inattentive type and predominantly hyperactive—impulsive type; attention deficit/hyperactivity disorder NOS; conduct disorder, oppositional defiant disorder and disruptive behavior disorder NOS), substance related disorders, eating disorders such as anorexia and bulimia.

In certain embodiments, compounds of Formulae I-II and pharmaceutically acceptable salts thereof are useful in treatment, prevention, amelioration or management of diseases or disorders, including, but not limited to disorders of central nervous system, such as epilepsy, ischaemic or hemorrhagic cerebral vascular accidents, neurodegenerative diseases, such as Charcot-Marie-Tooth disease or Friedreich disease, phakomatoses, in particular neurofibromatoses, neuropathic diseases, such as deficiency neuropathy, in particular of the alcoholic kind, toxic or drug-induced neuropathy, particularly by vincristine, neuropathy associated with a metabolic disturbance such as diabetes, neuropathy associated with an inflammatory process, in particular Guillain-Barre syndrome, infectious neuropathic diseases, in particular Herpes zoster, and radiculoneuropathic diseases, paraneoplastic polyneuritis, multiple sclerosis, amyotrophic lateral sclerosis, spinal muscular atrophy, schizophrenia, depression, brain tumours, Parkinson's disease, and dementias, such as Alzheimer's disease, Pick's disease or vascular dementia, multiple sclerosis, nerve regeneration, neurodegenerative diseases, muscle relaxation in spinal spasticity, cerebral palsy, trigeminal neuralgia, migraine, Alzheimer's disease, pain, drug withdrawal symptoms and convulsive disorders such as epilepsy.

In certain embodiments, compounds or compositions of this invention are useful in treatment of mental disorders, such as anxiety, depression, epilepsy, obsessive compulsive disorders, attention deficit disorder (ADD), attention deficit disorder with hyperactivity (ADHD), sleep disorders, eating disorders such as anorexia and bulimia, panic attacks, and other mental disorders.

In some embodiments, the central system disorder is selected from multiple sclerosis, muscle relaxation in spinal spasticity, cerebral palsy, trigeminal neuralgia, migraine, Alzheimer's disease, Huntington's chorea, Parkinson's disease, Creutzfeldt-Jakob's disease, neurodegenerative diseases, delirium, dementia, amnestic disorders, cognitive disorders; ischemic or hemorrhagic cerebral vascular incidents including stroke and traumatic brain injury (TBI), phacomatoses, amyotrophic lateral sclerosis, spinal muscular atrophy, schizophrenia, mood disorders, depression, drug withdrawal, symptoms, stuttering, autism, autism spectrum disorders, convulsive disorders, epilepsy, anxiety disorders, sleep disorders, attention deficit disorder, attention deficit hyperactivity disorder, disruptive behavior disorders, and substance related disorders.

In some embodiments the compounds of Formulae I-II are used to treat neuropathic disorders is selected from diabetic neuropathy, drug-induced neuropathy, inflammatory neuropathy, peripheral neuropathy, HIV-induced neuralgia and post-herpetic neuralgia, neuropathies associated with enzyme deficiency as in Fabry's disease and Krabbe's disease, hereditary motor and sensory neuropathies such as Charcot-Marie-Tooth disease.

In some embodiments the compounds of Formulae I-II are used to treat central nervous system disorders selected from cognitive disorders, delirium; dementia, dementia of Alzheimer's type, vascular dementia, dementia due to HIV disease, dementia due to head trauma, dementia due to Parkinson's disease, dementia due to Huntington's disease, dementia due to Pick's disease, dementia due to Creutzfeldt-Jakob disease, and amnestic disorders.

In some embodiments the compounds of Formulae I-II are used to treat multiple sclerosis.

In some embodiments the compounds of Formulae I-II are used to treat epilepsy.

In some embodiments the compounds of Formulae I-II are used to treat central nervous system disorders is selected from anxiety disorders, panic disorder without agoraphobia, panic disorder with agoraphobia, agoraphobia without history of panic disorder, specific phobia, social phobia, obsessive compulsive disorder, post-traumatic stress disorder, acute stress disorder, generalized anxiety disorder, anxiety disorder due to a medical condition, substance induced anxiety disorder, and anxiety disorder not otherwise specified (NOS).

In some embodiments the compounds of Formulae I-II are used to treat amyotrophic lateral sclerosis.

In some embodiments the compounds of Formulae I-II are used to treat spinal muscular atrophy.

In some embodiments the compounds of Formulae I-II are used to treat central nervous system disorders selected from mood disorders, depressive disorder, including major depressive disorder—single episode or recurrent, dysthymic disorder, depressive disorder NOS; bipolar disorder, including. bipolar I disorder, bipolar II disorder, cyclothymic disorder, bipolar disorder NOS, mood disorder due to general medical condition, substance-induced mood disorder, and mood disorder NOS.

In some embodiments the compounds of Formulae I-II are used to treat inflammatory disorders. In one aspect, the inflammatory disorder is rheumatoid arthritis.

In some embodiments the compounds of Formulae I-II are used to treat gut motility disorders. In one aspect, the gut motility disorder is irritable bowel syndrome.

In certain embodiments, compounds of Formulae I-II are useful in treatment of diseases or disorders, including, but not limited to cardiovascular disorders such as hypertension.

In certain embodiments, compounds of Formulae I-II are useful as an analgesic or antidepressant.

In certain embodiments, compounds of Formulae I-II are useful in the treatment or prevention retinal degenerations and photo-induced damage to the retina including photoretinitis, retinitis pigmentosa, age-related macular degeneration (AMD) and macular degeneration.

Combination Therapy

In certain embodiments, compounds of Formulae I-II provided herein are administered in combination with one or more other active ingredients, such as other agents effective for CNS disorders or mental disorders. Such agents include, but are not limited to the following: serotonin receptor (including., 5-HT1A) agonists and antagonists; neurokinin receptor antagonists or corticotropin releasing factor receptor (CRF1) antagonists; melatonin receptor agonists; and nicotinic agonists, muscarinic agents, acetylcholinesterase inhibitors and dopamine receptor agonists.

In certain embodiments, the other active agents are arylpiperazines, for example buspirone, gepirone, ipsapirone and tondospirone; benzodiazepine derivatives such as alprazolam, bromazepam, camazepam, chlordiazepoxide, clobazam, clorazepate, chotiazepam, cloxazolam, diazepam, ethyl loflazepate, etizolam, fluidazepam, flutazolam, flutoprazepam, halazepam, ketazolam, lorazepam, loxapine, medazepam, metaclazepam, mexazolam, nordazepam, oxazepam, oxazolam, pinazepam, prazepam and tofisopam; carbamates such as cyclarbamate, emylcamate, hydroxyphenamate, meprobamate, phenprobamate and tybamate; and others such as alpidem, benzoctamine, captodiamine, chlormezanone, flesinoxan, fluoresone, glutamic acid, hydroxyzine, lesopitron, mecloralurea, mephenoxalone, mirtazepine, oxanamide, phenaglycodol, suriclone and zatosetron.

In certain embodiments, the other active agent is fluoxetine, paroxetine, sertraline, citalopram, orfluvoxamine, venlafaxine, mirtazapine, nefazodone, trazodone, bupropion, lithium, valproic acid carbamazepine, neurontin, lamictal, ziprasidone, risperidone, quetiapine, phenelzine, tranylcypromine, amitriptyline, protriptyline, desipramine, nortriptyline, trimipramine, perphenazine, maprotiline, mirtazapine, methylphenidate or dextroamphetamine.

In certain embodiments, the other active agent is an antidepressant, such as a tricyclic antidepressant ("TCA"), a selective serotonin reuptake inhibitor ("SSRI"), a serotonin and noradrenaline reuptake inhibitor ("SNRI"), a dopamine reuptake inhibitor ("DRI"), a noradrenaline reuptake inhibitor ("NRI"), a dopamine and noradrenaline reuptake inhibitor ("DNRI"), a monoamine oxidase inhibitor ("MAOI"), an alpha-2-receptor blocker or another antidepressant.

Exemplary TCAs include, but are not limited to, amitriptyline, amoxapine, clomipramine, desipramine, doxepin, imipramine, maprotiline, nortriptyline, protriptyline, and trimipramine.

Exemplary SSRIs include, but are not limited to, sertraline, sertraline metabolite demethylsertraline, fluoxetine, norfluoxetine (fluoxetine desmethyl metabolite), fluvoxamine, paroxetine, citalopram, citalopram metabolite desmethylcitalopram, escitalopram, d,l-fenfluramine, femoxetine, ifoxetine, cyanodothiepin, litoxetine, cericlamine and dapoxetine.

Exemplary NRIs include, but are not limited to, reboxetine and all isomers of reboxetine, i.e., (R/R,S/S,R/S,S/R), desipramine, maprotiline, lofepramine, oxaprotiline, fezolamine, atomoxetine, nomifensine, viloxazine, or mianserin.

Exemplary SNRIs include, but are not limited to, venlafaxine, venlafaxine metabolite O-desmethylvenlafaxine, clomipramine, clomipramine metabolite desmethylclomipramine, duloxetine, milnacipran, imipramine, and nefazaodone.

Exemplary MAOIs include, but are not limited to, phenelzine, tranylcypromine, isocarboxazid, and selegiline.

Exemplary alpha-2-receptor blockers include, but are not limited to, mirtazapine.

Other useful antidepressants include buprorion, buprorion metabolite hydroxybuproprion and trazodone.

In one embodiment, in the methods provided herein, "compounds or compositions of this invention are used as an unsolvated or a free compound.

In another embodiment, in the methods provided herein, compounds or compositions of this invention are used as a salt, such as a hydrochloride salt.

In another embodiment, in the methods provided herein, compounds or compositions of this invention are used as a solvate.

Formulations

Compounds of the invention are administered orally in a total daily dose of about 0.01 mg/kg/dose to about 100 mg/kg/dose, alternately from about 0.1 mg/kg/dose to about 10 mg/kg/dose. The use of time-release preparations to control the rate of release of the active ingredient may be employed. The dose may be administered in as many divided doses as is convenient. When other methods are used (including. intravenous administration), compounds are administered to the affected tissue at a rate from 0.05 to 10 mg/kg/hour, alternately from 0.1 to 1 mg/kg/hour. Such rates are easily maintained when these compounds are intravenously administered as discussed below.

For the purposes of this invention, the compounds may be administered by a variety of means including orally, parenterally, by inhalation spray, topically, or rectally in formulations containing pharmaceutically acceptable carriers, adjuvants and vehicles. The term parenteral as used here includes subcutaneous, intravenous, intramuscular, and intraarterial injections with a variety of infusion techniques. Intraarterial and intravenous injection as used herein includes administration through catheters. Oral administration is generally employed.

Pharmaceutical compositions containing the active ingredient may be in any form suitable for the intended method of administration. When used for oral use for example, tablets, troches, lozenges, aqueous or oil suspensions, dispersible powders or granules, emulsions, hard or soft capsules, syrups or elixirs may be prepared. Compositions intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, calcium or sodium phosphate; granulating and disintegrating agents, such as maize starch, or alginic acid; binding agents, such as starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax maybe employed.

Formulations for oral use may be also presented as hard gelatin capsules where the active ingredient is mixed with an inert solid diluent, for example calcium phosphate or kaolin, or as soft gelatin capsules wherein the active ingredient is mixed with water or an oil medium, such as peanut oil, liquid paraffin or olive oil.

Aqueous suspensions of the invention contain the active materials in admixture with excipients suitable for the manufacture of aqueous suspensions. Such excipients include a suspending agent, such as sodium carboxymethylcellulose, methylcellulose, hydroxypropyl methylcellulose, sodium alginate, polyvinylpyrrolidone, gum tragacanth and gum acacia, and dispersing or wetting agents such as a naturally occurring phosphatide (including., lecithin), a condensation product of an alkylene oxide with a fatty acid (including., polyoxyethylene stearate), a condensation product of ethylene oxide with a long chain aliphatic alcohol (including., heptadecaethyleneoxycetanol), a condensation product of ethylene oxide with a partial ester derived from a fatty acid and a hexitol anhydride (including., polyoxyethylene sorbitan monooleate). The aqueous suspension may also contain one or more preservatives such as ethyl or n-propyl p-hydroxy-benzoate, one or more coloring agents, one or more flavoring agents and one or more sweetening agents, such as sucrose or saccharin.

Oil suspensions may be formulated by suspending the active ingredient in a vegetable oil, such as arachis oil, olive oil, sesame oil or coconut oil, or in a mineral oil such as liquid paraffin. The oral suspensions may contain a thickening agent, such as beeswax, hard paraffin or cetyl alcohol. Sweetening agents, such as those set forth above, and flavoring agents may be added to provide a palatable oral preparation. These compositions may be preserved by the addition of an antioxidant such as ascorbic acid.

Dispersible powders and granules of the invention suitable for preparation of an aqueous suspension by the addition of water provide the active ingredient in admixture with a dispersing or wetting agent, a suspending agent, and one or more preservatives. Suitable dispersing or wetting agents and suspending agents are exemplified by those disclosed above. Additional excipients, for example sweetening, flavoring and coloring agents, may also be present.

The pharmaceutical compositions of the invention may also be in the form of oil-in-water emulsions. The oily phase may be a vegetable oil, such as olive oil or arachis oil, a mineral oil, such as liquid paraffin, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan monooleate, and condensation products of these partial esters with ethylene oxide, such as polyoxyethylene sorbitan monooleate. The emulsion may also contain sweetening and flavoring agents.

Syrups and elixirs may be formulated with sweetening agents, such as glycerol, sorbitol or sucrose. Such formulations may also contain a demulcent, a preservative, a flavoring or a coloring agent.

The pharmaceutical compositions of the invention may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such as a solution in 1,3-butanediol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

The amount of active ingredient that may be combined with the carrier material to produce a single dosage form will vary depending upon the host treated and the particular mode of administration. For example, a time-release formulation intended for oral administration to humans may contain approximately 1 to 1000 mg of active material compounded with an appropriate and convenient amount of carrier material which may vary from about 5 to about 95% of the total compositions. The pharmaceutical composition can be prepared to provide easily measurable amounts for administration. For example, an aqueous solution intended for intravenous infusion should contain from about 3 to 330 μg of the active ingredient per milliliter of solution in order that infusion of a suitable volume at a rate of about 30 mL/hr can occur.

As noted above, formulations of the present invention suitable for oral administration may be presented as discrete units such as capsules, cachets or tablets each containing a predetermined amount of the active ingredient; as a powder or granules; as a solution or a suspension in an aqueous or non-aqueous liquid; or as an oil-in-water liquid emulsion or a water-in-oil liquid emulsion. The active ingredient may also be administered as a bolus, electuary or paste.

A tablet may be made by compression or molding, optionally with one or more accessory ingredients. Compressed tablets may be prepared by compressing in a suitable machine the active ingredient in a free flowing form such as a powder or granules, optionally mixed with a binder (including., povidone, gelatin, hydroxypropylmethyl cellulose), lubricant, inert diluent, preservative, disintegrant (including., sodium starch glycolate, cross-linked povidone, cross-linked sodium carboxymethyl cellulose) surface active or dispersing agent. Molded tablets may be made by molding in a suitable machine a mixture of the powdered compound moistened with an inert liquid diluent. The tablets may optionally be coated or scored and may be formulated so as to provide slow or controlled release of the active ingredient therein using, for example, hydroxypropyl methylcellulose in varying proportions to provide the desired release profile. Tablets may optionally be provided with an enteric coating, to provide release in parts of the gut other than the stomach. This is particularly advantageous with the compounds of Formula I when such compounds are susceptible to acid hydrolysis.

Formulations suitable for topical administration in the mouth include lozenges comprising the active ingredient in a flavored base, usually sucrose and acacia or tragacanth; pastilles comprising the active ingredient in an inert base such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous isotonic sterile injection solutions which may contain antioxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose sealed containers, for example, ampoules and vials, and may be stored in a freeze-dried (lyophilized) condition requiring only the addition of the sterile liquid carrier, for example water for injections, immediately prior to use. Injection solutions and suspensions may be prepared from sterile powders, granules and tablets of the kind previously described.

Suitable unit dosage formulations are those containing a daily dose or unit, daily sub-dose, or an appropriate fraction thereof, of a compound of Formula I.

The formulations of the present invention may include any of the compounds of Formula I or pharmaceutically acceptable salts, solvates or prodrugs thereof as the only pharmaceutically active agent. Alternatively, the formulations may include one or more further active agents including those described under the section Combination Therapy.

It will be understood, however, that the specific dose level for any particular patient will depend on a variety of factors including the activity of the specific compound employed; the age, body weight, general health, sex and diet of the individual being treated; the time and route of administration; the rate of excretion; other drugs which have previously been administered; and the severity of the particular disease undergoing therapy, as is well understood by those skilled in the art.

The invention also provides a kit comprising a therapeutically effective amount of a compound of Formula I, or a pharmaceutically acceptable salt, solvate, or prodrug thereof, and instructions for treating a human patient suffering from conditions amenable to modulation of the $GABA_A$ receptor complex; or increasing endogenous neurosteroid and neuroactive steroid levels; CNS disorders; PNS disorders; or inflammatory conditions as described above. The kit may also include one or more further active agents including those described under the section Combination Therapy.

SYNTHETIC CHEMISTRY EXAMPLES

Standard procedures and chemical transformation and related methods are well known to one skilled in the art, and such methods and procedures have been described, for example, in standard references such as Fiesers' Reagents for Organic Synthesis, John Wiley and Sons, New York, N.Y., 2002; Organic Reactions, vols. 1-83, John Wiley and Sons, New York, N.Y., 2006; March J. and Smith M.: Advanced Organic Chemistry, 6th ed., John Wiley and Sons, New York, N.Y.; and Larock R. C.: Comprehensive Organic Transformations, Wiley-VCH Publishers, New York, 1999.

Reactions using compounds having functional groups may be performed on compounds with functional groups that may be protected. A "protected" compound or derivatives means derivatives of a compound where one or more reactive site or sites or functional groups are blocked with protecting groups. Protected derivatives are useful in the preparation of the compounds of the present invention or in themselves; the protected derivatives may be the biologically active agent. An example of a comprehensive text listing suitable protecting groups may be found in T. W. Greene, *Protecting Groups in Organic Synthesis,* 3rd edition, John Wiley & Sons, Inc. 1999.

A compound of Formulae I-II can be synthesized as depicted in scheme 1:

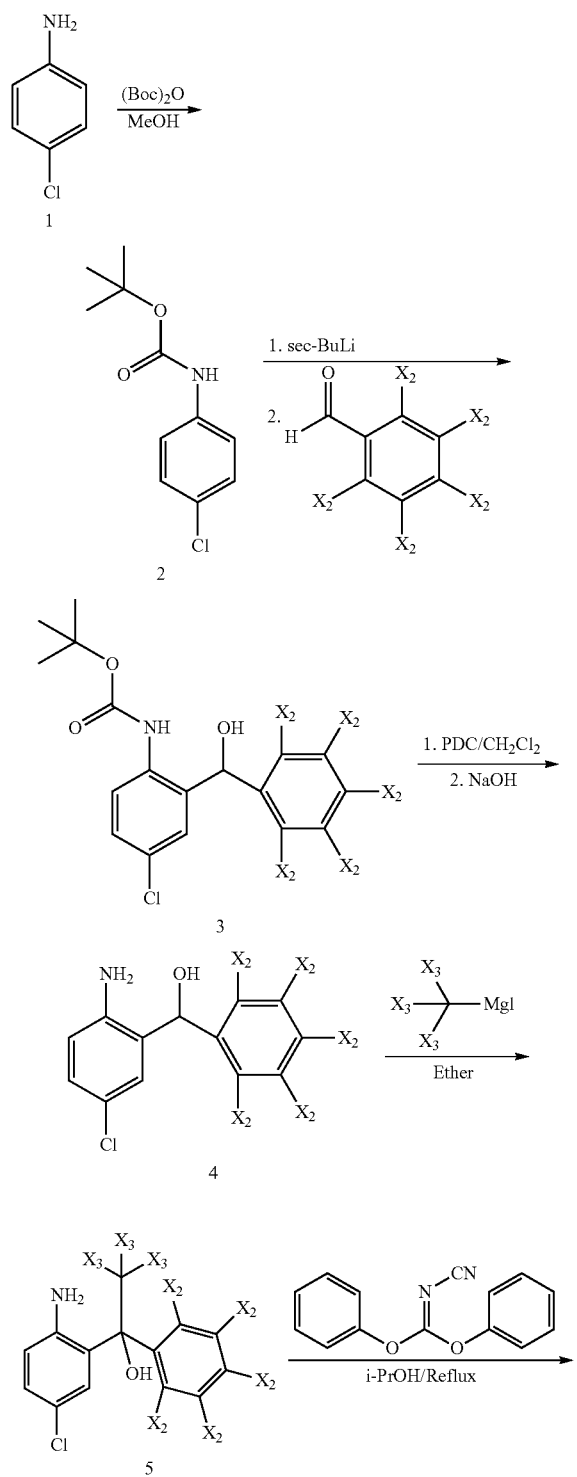

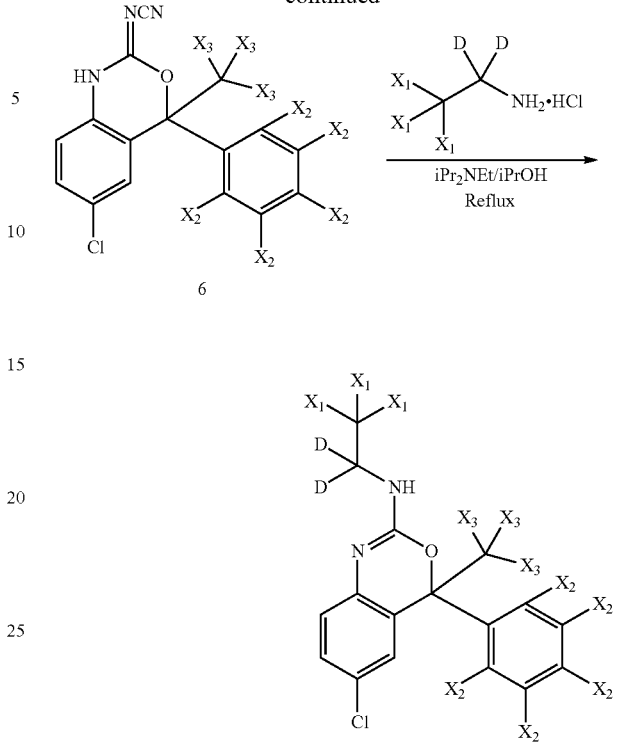

$X_1, X_2, X_3$ are independently selected from deuterium or hydrogen

Protection of the amino group of p-Chloro aniline 1 by means known in the art is achieved by treating the amine 1 with Di-t-Butyl dicarbonate. As described by E. Azim et al. in *J. Label. Compds. Radiopharm.* XXXIX:907, 1997, ortho lithiation of 2 followed by addition of benzaldehyde yields the tertiary alcohol 3. Further benzylic oxidation of 3 followed by hydrolytic cleavage of the amino protective group provides compound 4. Addition of methyl Grignard in diethyl ether yields the tertiary alcohol 5. As described by Garratt, P. J et al. in *Tetrahedron,* 45 (3), 829, 1989, Alcohol 5 is reacted with diphenyl cyanocarbonimidate to give compound 6. Further reaction with deuterated ethylamine in refluxing isopropyl alcohol yields compounds of Formula I.

A compound of Formulae I-II can also be synthesized from intermediate 5 as depicted in scheme 2:

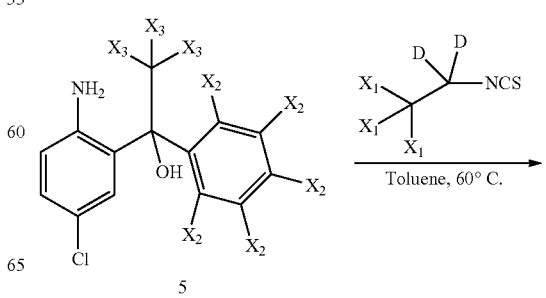

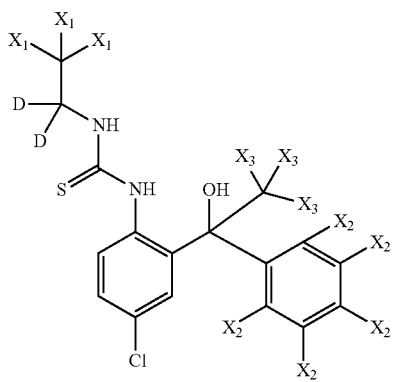

7

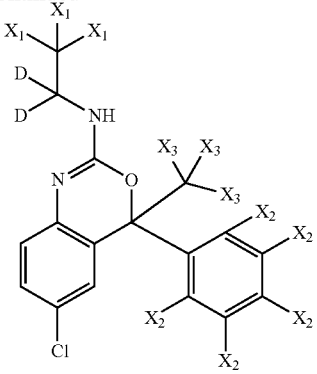

Formula I

X₁, X₂, X₃ are independently selected from deuterium or hydrogen

As described by E. Azim et al. in *J. Label. Compds. Radiopharm.* XXXIX:907, 1997, treating intermediate 5 with deuterated ethyl isothiocyanate at 60° C. in toluene yields the thiourea 7. As described by S-W You et al. in *Bull. Korean Chem. Soc.* 2001, (22), 11, 1270, thiourea 7 is reacted with dicyclohexylcarbodiimide in refluxing acetonitrile to yield compounds of Formula I.

The Compound numbers correspond to the Example numbers provided in Table 1 below.

TABLE 1

| Example number | Example name | Example Structure |
|---|---|---|
| 1 | 6-chloro-N-(ethyl-d₅)-4-methyl-4-phenyl-4H-3,1-benzoxazin-2-amine | |
| 2 | 6-chloro-N-(ethyl-d₅)-4-methyl-4-(phenyl-d₅)-4H-3,1-benzoxazin-2-amine | |

TABLE 1-continued

| Example number | Example name | Example Structure |
|---|---|---|
| 3 | 6-chloro-N-(ethyl-d$_5$)-4-(methyl-d$_3$)-4-(phenyl-d$_5$)-4H-3,1-benzoxazin-2-amine | |
| 4 | 6-chloro-N-(ethyl-1,1-d2)-4-methyl-4-phenyl-4H-3,1-benzoxazin-2-amine | |
| 5 | 6-chloro-N-ethyl-4-(methyl-d3)-4-(phenyl-d5)-4H-3,1-benzoxazin-2-amine | |
| 6 | 6-chloro-N-ethyl-4-methyl-4-(phenyl-d5)-4H-3,1-benzoxazin-2-amine | |

TABLE 1-continued

| Example number | Example name | Example Structure |
|---|---|---|
| 7 | 6-chloro-N-ethyl-4-(methyl-d3)-4-phenyl-4H-3,1-benzoxazin-2-amine | |

Example 1

Synthesis of 6-chloro-N-(ethyl-$d_5$)-4-methyl-4-phenyl-4H-3,1-benzoxazin-2-amine

Synthesis of 1-(2-amino-5-chlorophenyl)-1-phenyethan-1-ol

To 2-amino-5-chlorobenzophenone (2.34 mmols, 541 mgs) in diethyl ether (10 mL) under nitrogen atmosphere at 0° C. was added dropwise methylmagnesium iodide (3.12 mL, 3.0M in diethyl ether). The reaction mixture was stirred and left to warm to room temperature. After 5 hours, the mixture was cooled to 0° C. and ice chips were carefully added followed by cold water. Brine was added to separate the phases. The ether layer was separated. The aqueous layer was extracted with an equal amount of ether. The combined ether layers were dried over magnesium sulfate, filtered and concentrated under vacuum to yield the tertiary alcohol (2.14 mmols, 530 mgs). MS: (M+H) 248.

Synthesis of N-(6-chloro-4-methyl-4-phenyl-1,4-dihydro-2H-benzo[d][1,3]oxazin-2-ylidene)cyanamide Diphenyl cyanocarbonimidate (10.3 mmols, 2.53 g) and 1-(2-amino-5-chlorophenyl)-1-phenyethan-1-ol (9.36 mmols, 2.32 g) were added to isopropanol (40 mL) and the reaction mixture was refluxed for 24 hours under nitrogen atmosphere. The solvent was removed under vacuum and the residue was purified by flash chromatography (silica gel) (Eluent 2% MeOH/CH$_2$CL$_2$) to yield N-(6-chloro-4-methyl-4-phenyl-1,4-dihydro-2H-benzo[d][1,3]oxazin-2-ylidene)cyanamide as a white solid (2.7 mmols, 800 mgs). MS: (M−) 296.

Synthesis of 6-chloro-N-(ethyl-$d_5$)-4-methyl-4-phenyl-4H-3,1-benzoxazin-2-amine $d_5$-ethylamine hydrochloride (0.69 mmols, 59 mgs) (99% deuterium incorporation) was added to a flask containing N-(6-chloro-4-methyl-4-phenyl-1,4-dihydro-2H-benzo[d][1,3]oxazin-2-ylidene)cyanamide (100 mgs, 0.35 mmol) and Hunig's base (0.7 mmol, 0.12 mL) in isopropanol (1 mL). The mixture was stirred at reflux for 12 hours. Additional $d_5$-ethylamine hydrochloride (0.69 mmol, 59 mgs) and Hunig's base (0.7 mmol, 0.12 mL) were added and the reaction mixture was stirred at reflux for another 12 hours. The solvent was then removed under vacuum and the residue purified by reverse phase (Agilent C18 eclipse plus column) HPLC to yield 6-chloro-N-(ethyl-$d_5$)-4-methyl-4-phenyl-4H-3,1-benzoxazin-2-amine (0.11 mmols, 33 mgs) as a waxy solid. MS: (M+H) 306.

Example 2

Synthesis of 6-chloro-N-(ethyl-$d_5$)-4-methyl-4-(phenyl-$d_5$)-4H-3,1-benzoxazin-2-amine

Synthesis of tert-butyl (4-chloro-2-(hydroxy(phenyl-d5)methyl)phenyl)carbamate A solution of tert-butyl (4-chlorophenyl)carbamate (2.03 g, 8.92 mmols) dissolved in 52 mL of dry THF at −78° C. was treated with 16 mL (22.4 mmol, 2.5 eq.) of a 1.4M solution of sec-butyllithium in cyclohexane added via syringe over 25 min. The reaction mixture was allowed to warm to −25° C. and was treated with $d_6$-benzaldehyde (900 µL) (98% deuterium incorporation). Upon addition, the reaction mixture was allowed to warm to room temperature. The reaction mixture was then cooled to 0° C., quenched with 26 mL of a saturated aqueous NH$_4$Cl solution and 50 mL of water. The aqueous layer was washed with EtOAc (50 mL). Pooled organic layers were washed with brine, dried over MgSO$_4$, filtered and concentrated to give 3.4 g of a yellow oil. The residual oil was purified by flash silica gel chromatography (4:1 hexanes/EtOAc) to yield tert-butyl (4-chloro-2-(hydroxy(phenyl-$d_5$)methyl)phenyl)carbamate as a yellow oil (2.45 g, 7.24 mmols). MS: (M+H) 339.

Synthesis of tert-butyl (2-(benzoyl-2,3,4,5,6-d5)-4-chlorophenyl)carbamate

A solution of tert-butyl (4-chloro-2-(hydroxy(phenyl-d5)methyl)phenyl)carbamate (1.5 g, 4.41 mmol) was dissolved in 40 mL of CH$_2$Cl$_2$ and treated with NaOAc (1.14 g), Celite (1.82 g) and PCC (1.48 g) added in portions. The resulting mixture was stirred at room temperature for 90 minutes. An additional 500 mg of PCC was added and stirred for an additional hour. The reaction mixture was loaded on a silica gel column and eluted with CH$_2$Cl$_2$. The collected fractions were evaporated to give tert-butyl (2-(benzoyl-2,3,4,5,6-d5)-4-chlorophenyl)carbamate (1.12 g, 3.33 mmols). MS: (M+H) 337.

Synthesis of (2-amino-5-chlorophenyl)(phenyl-d5)methanone

A solution of tert-butyl (2-(benzoyl-2,3,4,5,6-d5)-4-chlorophenyl)carbamate (1.05 g, 3.12 mmol) in EtOH (17 mL) was treated with a 10% NaOH (2.5 M; 3.4 mL) aqueous solution added dropwise. The mixture was then refluxed for 24 hours. An additional 3 mL of 2.5 N NaOH was added and the reaction mixture was refluxed for an additional 7 hours. After cooling to room temperature, the organic solvent removed in vacuo. The residue was diluted with ice-water. It was extracted with 75 mL of EtOAc. The phases were separated. The aqueous layer was extracted with EtOAc (2×40 mL). The combined organic layers were washed with water (50 mL, brine added to separate phases) and brine. After drying (MgSO$_4$), the mixture was filtered and concentrated in vacuo. To yield a red-orange oil that solidified on standing (730 mg). The crude reaction mixture was purified by flash silica gel chromatography eluting with 100% CH$_2$Cl$_2$. The product was obtained as a yellow-orange solid (610 mgs, 2.58 mmols). MS: (M+H) 237

Synthesis of 1-(2-amino-5-chlorophenyl)-1-(phenyl-d5)ethan-1-ol

To 2-amino-5-chlorobenzophenone (1.7 mmols, 402 mgs) in diethyl ether (10 mL) under nitrogen atmosphere at 0° C. was added dropwise methylmagnesium iodide (6.8 mL, 3.0M in diethyl ether). The reaction mixture was stirred and left to warm to room temperature. After 1.5 hour, the mixture was cooled to 0° C. and ice chips were carefully added followed by cold water. Brine was added to separate the phases. The ether layer was separated. The aqueous layer was extracted with an equal amount of ether. The combined ether layers were dried over magnesium sulfate, filtered and concentrated under vacuum to yield the tertiary alcohol (1.33 mmols, 335 mgs). MS: (M+H) 253.

Synthesis of 1-(4-chloro-2-(1-hydroxy-1-(phenyl-d5)ethyl)phenyl)-3-(ethyl-d5)thiourea To 1-(2-amino-5-chlorophenyl)-1-(phenyl-d5)ethan-1-ol (167 mgs, 0.67 mmols) in toluene (3 mL) was added with d5-ethyl isothiocyanate (0.99 mmol, 88 µL). The mixture was stirred at 60° C. for 24 hours. The solvent was removed in vacuo and the residue was purified by flash silica gel chromatography eluting with 3/1 hexanes/EtOAc to yield the product (0.6 mmol, 204 mgs) MS: (M+H) 340.

Synthesis of d$_5$-ethyl isothiocyanate

Ethyl d$_5$-ethyldithiocarbamate d$_5$-ethylamine hydrochloride salt (1.27 g, 14.7 mmols) (99% deuterium incorporation) was suspended in EtOH-free CHCl$_3$ (8 mL) and cooled in an ice water bath and treated with neat Et$_3$N (4.1 mL, 29.4 mmols) added dropwise via syringe. Neat CS$_2$ (969 µL, 16.2 mmols) was added dropwise via syringe and the cold bath was removed. The thick mixture stirred at room temperature for 3 h and cooled in an ice-salt bath to −10° C. Neat iodoethane (1.2 mL, 15.0 mmols) was added to the cold reaction mixture dropwise via syringe. The reaction mixture was allowed to warm to room temperature and stirred overnight. The resulting solution was concentrated in vacuo and the residue was treated with 60 mL each of EtOAc and a 1M HCl solution. The organic layer was washed with water (40 mL), dried (MgSO$_4$), filtered and concentrated in vacuo, affording 2.07 g of a brown oil.

d$_5$-Ethyl isothiocyanate

A flask equipped with a distillation head containing ethyl d$_5$-ethyldithiocarbamate was placed in a sand bath at 150° C. and heated to 230° C. A light yellow liquid was collected as it distilled off. This liquid was heated at 80° C. to remove ethanethiol leaving d$_5$-ethyl isothiocyanate as a light yellow liquid.

Synthesis of (6-chloro-N-(ethyl-d5)-4-methyl-4-(phenyl-d5)-4H-3,1-benzoxazin-2-amine To a stirred solution of 1-(4-chloro-2-(1-hydroxy-1-(phenyl-d5)ethyl)phenyl)-3-(ethyl-d5)thiourea (100 mgs, 0.29 mmol) in acetonitrile (2 mL) was added dicyclohexylcarbodiimide (0.45 mmol, 91 mgs). The reaction mixture was heated to reflux for 3 hours. The solvent was evaporated and the residue was purified by flash silica gel chromatography eluting with 85/15 hexanes/EtOAc to yield (6-chloro-N-(ethyl-d5)-4-methyl-4-(phenyl-d5)-4H-3,1-benzoxazin-2-amine. MS: (M+H) 311.

Example 3

Synthesis of 6-chloro-N-(ethyl-d$_5$)-4-(methyl-d$_3$)-4-(phenyl-d$_5$)-4H-3,1-benzoxazin-2-amine Following the same steps described in example 2 and substituting methylmagnesium iodide with d$_3$-methylmagnesium iodide (prepared from d$_3$-iodomethane 99.5% deuterium incorporation) provides 6-chloro-N-(ethyl-d$_5$)-4-(methyl-d$_3$)-4-(phenyl-d$_5$)-4H-3,1-benzoxazin-2-amine. MS: (M+H) 314.

Example 4

Synthesis of 6-chloro-N-(ethyl-1,1-d2)-4-methyl-4-phenyl-4H-3,1-benzoxazin-2-amine Following the same steps described in example 1 and substituting d$_5$-ethylamine hydrochloride with 1,1-d$_2$-ethylamine hydrochloride (98% deuterium incorporation) provides 6-chloro-N-(ethyl-1,1-d2)-4-methyl-4-phenyl-4H-3,1-benzoxazin-2-amine. MS: (M+H) 303.

Example 5

Synthesis of 6-chloro-N-ethyl-4-(methyl-d3)-4-(phenyl-d5)-4H-3,1-benzoxazin-2-amine Following the same steps described in example 2 and substituting d$_5$-ethylisothiocyanate with ethylisothiocyanate and substituting methylmagnesium iodide with d$_3$-methylmagnesium iodide provides 6-chloro-N-ethyl-4-(methyl-d3)-4-(phenyl-d5)-4H-3,1-benzoxazin-2-amine. MS: (M+H) 309.

Example 6

Synthesis of 6-chloro-N-ethyl-4-methyl-4-(phenyl-d5)-4H-3,1-benzoxazin-2-amine Following the same steps described in example 2 and substituting d$_5$-ethylisothiocyanate with ethylisothiocyanate provides 6-chloro-N-ethyl-4-methyl-4-(phenyl-d5)-4H-3,1-benzoxazin-2-amine. MS: (M+H) 306.

Example 7

Synthesis of 6-chloro-N-ethyl-4-(methyl-d3)-4-phenyl-4H-3,1-benzoxazin-2-amine

Following the same steps described in example 2 and substituting $d_5$-ethylisothiocyanate with ethylisothiocyanate and substituting methylmagnesium iodide with $d_3$-methylmagnesium iodide and substituting $d_6$-benzaldehyde with benzaldehyde provides 6-chloro-N-ethyl-4-(methyl-d3)-4-phenyl-4H-3,1-benzoxazin-2-amine. MS: (M+H) 304.

Example 8

Synthesis of 6-chloro-N-(ethyl-d5)-4-(methyl-d3)-4-phenyl-4H-3,1-benzoxazin-2-amine Following the same steps described in example 1 and substituting methylmagnesium iodide with $d_3$-methylmagnesium iodide provides 6-chloro-N-(ethyl-d5)-4-(methyl-d3)-4-phenyl-4H-3,1-benzoxazin-2-amine.

Example 9

Synthesis of 6-chloro-N-(ethyl-1,1-d2)-4-methyl-4-(phenyl-d5)-4H-3,1-benzoxazin-2-amine Following the same steps described in example 2 and substituting $d_5$-ethylisothiocyanate with 1,1-$d_2$-ethylisothiocyanate (prepared from 1,1-$d_2$-ethylamine hydrochloride (98% deuterium incorporation)) provides 6-chloro-N-(ethyl-1,1-d2)-4-methyl-4-(phenyl-d5)-4H-3,1-benzoxazin-2-amine.

Example 10

Synthesis of 6-chloro-N-(ethyl-1,1-d2)-4-(methyl-d3)-4-(phenyl-2-d)-4H-3,1-benzoxazin-2-amine Following the same steps described in example 1 and substituting methylmagnesium iodide with $d_3$-methylmagnesium iodide and $d_5$-ethylamine hydrochloride with 1,1-$d_2$-ethylamine hydrochloride (prepared from 1,1-$d_2$-iodoethane (98% deuterium incorporation)) provides 6-chloro-N-(ethyl-1,1-$d_2$)-4-(methyl-$d_3$)-4-(phenyl-$d_2$)-4H-3,1-benzoxazin-2-amine.

Example 11

Synthesis of 6-chloro-N-(ethyl-$d_2$)-4-(methyl-$d_3$)-4-(phenyl-$d_5$)-4H-3,1-benzoxazin-2-amine Following the same steps described in example 3 and substituting $d_5$-ethyl-isothiocyanate with 1,1-$d_2$-ethylisothiocyanate provides 6-chloro-N-(ethyl-1,1-$d_2$)-4-(methyl-$d_3$)-4-(phenyl-$d_5$)-4H-3,1-benzoxazin-2-amine.

BIOLOGICAL EXAMPLES

A. Evaluation of Metabolic Stability

Compounds were evaluated for liver microsome metabolic stability at Eurofins/Cerep (St. Charles, Mo.). Standard conditions for Cerep's liver microsome stability assay as described by Obach et al in *J. Pharmacol. Exp. Ther.* 283, 46, 1997, were used. Test compounds at a concentration of 0.1 µM were incubated for up to 60 minutes in duplicate. The microsomal protein concentration was 0.1 mg/mL. The parent compound was detected by HPLC-MS/MS analysis. The percent compound remaining was calculated by comparing the peak area of the parent compound at each time point to time zero. Half-life was estimated from the slope of the initial linear range of the logarithmic curve of parent compound remaining vs. time, assuming first order kinetics. The apparent intrinsic clearance was further calculated from the half-life value for assays with microsomes.

The results of the liver human microsomes stability study are shown in Table 2 below:

TABLE 2

| Compound | Half-life (minutes) | | |
|---|---|---|---|
| | Experiment 1 | Experiment 2 | Average |
| Etifoxine | 23 | 21.9 | 22 |
| Example 1 | 39.7 | 41.8 | 41 |

The compounds described as examples 6 and 7 were tested under the same conditions, but with a different lot of human liver microsomes. Both displayed an average half-life of 18 minutes.

The results of the rat liver microsomes stability study are shown in Table 3 below:

TABLE 3

| Compound | Half-life (minutes) | | |
|---|---|---|---|
| | Experiment 1 | Experiment 2 | Average |
| Etifoxine | 7.7 | 7.4 | 8 |
| Example 1 | 13.8 | 13.8 | 14 |

The results of the liver human microsome stability study reveal that the half-life of Example 1 is about 86% longer than that of etifoxine.

The results of the rat liver microsome stability study reveal that the half-life of Example 1 is about 75% longer than that of etifoxine.

B. Evaluation of Pharmacokinetics in Rats for Compound Example 1

Compounds were evaluated for pharmacokinetic profiles in male Sprague-Dawley rats at Shanghai Chempartner, Shanghai, China. Etifoxine hydrochloride and the hydrochloride salt of the compound described in example 1 were dosed to Sprague-Dawley rats via oral gavage (PO). Each compound was administered at a dose of 50 mg/kg to three rats (N=3 rats/compound; total 6 rats in the study). Each compound was formulated in 70/30 Saline/PEG400 at a concentration of 5 mg/mL (10 mL/kg injection volume/rat). Blood samples were collected from each rat at 10, 20, 30, 45 minutes and 1, 2, 4 and 12 hours post-dose. Blood samples were put on ice and centrifugated to obtain plasma. Plasma samples were analyzed for concentrations of the dosed compound at each time point by LC-MS/MS using an AB-Sciex API-400 mass spectrometer. The lower limit of quantitation of each compound was 1 ng/mL. Pharmacokinetic parameters were determined by non-compartmental analysis using WinNonlin 6.2 software.

FIG. 1. Shows averaged data for administered etifoxine hydrochloride and the hydrochloride salt of the compound described in example 1. Table 4, below, shows the average $AUC_{0-12}$ and $C_{max}$ observed for etifoxine hydrochloride and the hydrochloride salt of the compound described in example 1.

TABLE 4

| Compound | AUC$_{0-12}$ (hr*ng/mL) | C$_{max}$ (ng/mL) |
|---|---|---|
| Etifoxine hydrochloride | 3380 | 1140 |
| Example 1 hydrochloride | 8337 | 1930 |

As can be seen from table 4, the AUC$_{0-12}$ and C$_{max}$ of the hydrochloride salt of the compound described in example 1 are 2.5 times and 1.7 times greater than etifoxine hydrochloride. These results indicate decreased pre-systemic metabolism resulting in higher bioavailability of unmetabolized drug. Decreasing pre-systemic metabolism may result in lesser inter and intra-variability. Increasing drug exposure may result in reduced dosing frequency as minimal drug therapeutic level may be achieved for longer period of times. Increasing drug exposure also allows for dose lowering resulting in less potential adverse events as similar drug plasma levels can be achieved with a lower dose. The data on mean plasma concentration versus time are shown in FIG. 1.

The various features and embodiments of the present invention, referred to in individual sections above apply, as appropriate, to other sections, *mutatis mutandis*. Consequently features specified in one section may be combined with features specified in others sections, as appropriate.

The patents and publications listed herein describe the general skill in the art and are hereby incorporated by reference in their entireties for all purposes and to the same extent as if each was specifically and individually indicated to be incorporated by reference. In the case of any conflict between a cited reference and this specification, the specification shall control. In describing embodiments of the present application, specific terminology is employed for the sake of clarity. However, the invention is not intended to be limited to the specific terminology so selected. Nothing in this specification should be considered as limiting the scope of the present invention. All examples presented are representative and non-limiting. Without further description, it is believed that one of ordinary skill in the art can, using the preceding description and the illustrative examples, make and utilize the compounds of the present invention and practice the claimed methods. It is therefore to be understood that, within the scope of the claims and their equivalents, the invention may be practiced otherwise than as specifically described.

What is claimed is:
1. A compound of Formula II:

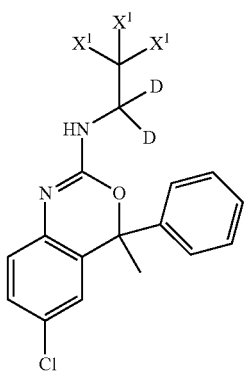

II or pharmaceutically acceptable salt thereof, wherein:
each X$^1$ is independently hydrogen or deuterium; or
a compound selected from the group consisting of:
6-chloro-N-(ethyl-d5)-4-methyl-4-phenyl-4H-3,1-benzoxazin-2-amine,
6-chloro-N-(ethyl-d5)-4-methyl-4-(phenyl-d5)-4H-3,1-benzoxazin-2-amine,
6-chloro-N-(ethyl-d5)-4-(methyl-d3)-4-(phenyl-d5)-4H-3,1-benzoxazin-2-amine,
6-chloro-N-(ethyl-1,1-d2)-4-methyl-4-phenyl-4H-3,1-benzoxazin-2-amine,
6-chloro-N-ethyl-4-(methyl-d3)-4-(phenyl-d5)-4H-3,1-benzoxazin-2-amine,
6-chloro-N-(ethyl-d5)-4-(methyl-d3)-4-phenyl-4H-3,1-benzoxazin-2-amine,
6-chloro-N-(ethyl-1,1-d2)-4-methyl-4-(phenyl-d5)-4H-3,1-benzoxazin-2-amine, and
6-chloro-N-(ethyl-1,1-d2)-4-(methyl-d3)-4-(phenyl-d5)-4H-3,1-benzoxazin-2-amine,
or a pharmaceutically acceptable salt thereof.

2. The compound of claim 1 wherein the compound is:
6-chloro-N-(ethyl-d5)-4-methyl-4-phenyl-4H-3,1-benzoxazin-2-amine,
6-chloro-N-(ethyl-d5)-4-methyl-4-(phenyl-d5)-4H-3,1-benzoxazin-2-amine,
6-chloro-N-(ethyl-d5)-4-(methyl-d3)-4-(phenyl-d5)-4H-3,1-benzoxazin-2-amine, and
6-chloro-N-(ethyl-1,1-d2)-4-methyl-4-phenyl-4H-3,1-benzoxazin-2-amine,
or a pharmaceutically acceptable salt thereof.

3. The compound of claim 1, wherein said compound is an enantiomerically pure S-etifoxine analog, or a pharmaceutically acceptable salt thereof.

4. The compound of claim 1, wherein any atom not designated as deuterium is present at its natural isotopic abundance.

5. A pharmaceutical composition comprising the compound of claim 1 and a pharmaceutically acceptable excipient.

6. A method of modulating the GABA$_A$ receptor complex in a subject in need thereof comprising administering to said subject an effective amount of the compound of claim 1.

7. A method of increasing endogenous neurosteroid and/or neuroactive steroid levels in a subject in need thereof comprising administering to said subject an effective amount of the compound of claim 1.

8. The compound of claim 1, wherein a deuterium is present at an abundance that is at least 3340 times greater than the natural abundance of deuterium.

9. The compound of claim 1, wherein said compound is an enantiomerically pure R-etifoxine analog, or a pharmaceutically acceptable salt thereof.

10. A compound which is 6-chloro-N-(ethyl-d5)-4-methyl-4-phenyl-4H-3,1-benzoxazin-2-amine) or a pharmaceutically acceptable salt thereof.

11. A pharmaceutical composition comprising the compound of claim 10 and a pharmaceutically acceptable excipient.

12. A method of modulating the GABA$_A$ receptor complex in a subject in need thereof comprising administering to said subject an effective amount of the compound of claim 10.

13. A method of increasing endogenous neurosteroid and/or neuroactive steroid levels in a subject in need thereof comprising administering to said subject an effective amount of the compound of claim 10.

14. The compound of claim 1 wherein the compound has Formula II:

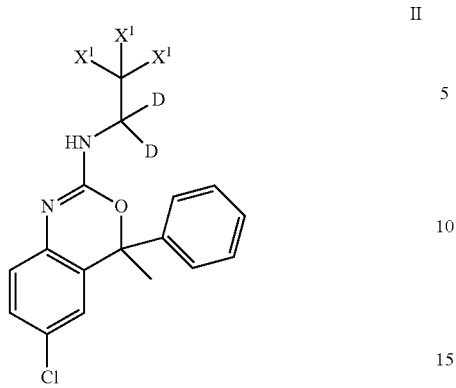

II or pharmaceutically acceptable salt thereof, wherein:
each $X^1$ is independently hydrogen or deuterium.

15. A pharmaceutical composition comprising the compound of claim 14 and a pharmaceutically acceptable excipient.

16. A method of modulating the $GABA_A$ receptor complex in a subject in need thereof comprising administering to said subject an effective amount of the compound of claim 14.

17. A method of increasing endogenous neurosteroid and/or neuroactive steroid levels in a subject in need thereof comprising administering to said subject an effective amount of the compound of claim 14.

* * * * *